US012180277B2

(12) United States Patent
Sharma et al.

(10) Patent No.: US 12,180,277 B2
(45) Date of Patent: Dec. 31, 2024

(54) LILRB4-BINDING ANTIBODY AND METHODS OF USE THEREOF

(71) Applicant: Board of Regents, The University of Texas System, Austin, TX (US)

(72) Inventors: Naveen Sharma, Houston, TX (US); James P. Allison, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 787 days.

(21) Appl. No.: 17/435,387

(22) PCT Filed: Mar. 2, 2020

(86) PCT No.: PCT/US2020/020651
§ 371 (c)(1),
(2) Date: Aug. 31, 2021

(87) PCT Pub. No.: WO2020/180789
PCT Pub. Date: Sep. 10, 2020

(65) Prior Publication Data
US 2022/0144944 A1 May 12, 2022

Related U.S. Application Data

(60) Provisional application No. 62/812,700, filed on Mar. 1, 2019.

(51) Int. Cl.
| | |
|---|---|
| *C07K 16/28* | (2006.01) |
| *A61K 39/00* | (2006.01) |
| *A61K 45/06* | (2006.01) |
| *A61P 35/00* | (2006.01) |
| *G01N 33/574* | (2006.01) |

(52) U.S. Cl.
CPC .......... *C07K 16/2803* (2013.01); *A61K 45/06* (2013.01); *A61P 35/00* (2018.01); *G01N 33/574* (2013.01); *A61K 39/00* (2013.01); *A61K 2039/505* (2013.01); *G01N 2333/70503* (2013.01)

(58) Field of Classification Search
CPC .......... C07K 16/2803; C07K 2317/33; C07K 2317/73; C07K 2317/76; A61K 45/06; A61K 2039/505; A61K 39/00; A61P 35/00; G01N 33/574; G01N 2333/70503
See application file for complete search history.

(56) References Cited

U.S. PATENT DOCUMENTS

| | | | |
|---|---|---|---|
| 7,777,008 B2 * | 8/2010 | Ponath | C07K 16/2803 |
| | | | 530/387.3 |
| 2007/0041982 A1 | 2/2007 | Ponath et al. | |
| 2009/0202544 A1 | 8/2009 | Suciu-Foca et al. | |
| 2017/0327591 A1 | 11/2017 | Suciu-Foca et al. | |

FOREIGN PATENT DOCUMENTS

| | | |
|---|---|---|
| WO | WO 2006/138739 | 12/2006 |
| WO | WO 2013/033734 | 3/2013 |
| WO | WO 2016/029079 | 2/2016 |
| WO | WO 2016/144728 | 9/2016 |
| WO | WO 2018/089300 | 5/2018 |
| WO | WO 2018/148494 | 8/2018 |

OTHER PUBLICATIONS

Boj, Sylvia F. et al., "Organoid Models of Human and Mouse Ductal Pancreatic Cancer," *Cell*; 160.0 (2015): 324-338.
English translation of Office Action issued in Chinese Patent Application No. 202080030789.9, dated Feb. 8, 2024.
English translation of Office Action issued in Japanese Application No. 2021-551767, dated Feb. 5, 2024.
English translation of Office Action issued in Japanese Application No. 2021-551767, dated Jun. 13, 2024.
Extended European Search Report issued in European Patent Application No. 20766187.7, dated Oct. 20, 2022.
Foster, Barbara A. et al., "Characterization of Prostatic Epithelial Cell Lines Derived from Transgenic Adenocarcinoma of the Mouse Prostate (TRAMP) Model," *Cancer Research* 57 (1997): 3325-3330.
PCT International Search Report and Written Opinion issued in International Patent Application No. PCT/US2020/020651, mailed Jun. 12, 2020.
PCT International Preliminary report on Patentability issued in International Patent Application No. PCT/US2020/020651, mailed Sep. 16, 2021.
R&D Systems. Human LILRB4/CD85k/ILT3 Antibody. Catalog No. MAB24251 (2018). [Retrieved on May 18, 2020]. Retrieved from the Internet: URL: https://resources.rndsystems.com/pdfs/datasheets/mab24251.pdf.
Van Elsas, Andrea et al., "Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation," Journal of Experimental Medicine 190.3 (1999): 355-366.

\* cited by examiner

*Primary Examiner* — Brad Duffy
*Assistant Examiner* — Amber K Faust
(74) *Attorney, Agent, or Firm* — Parker Highlander PLLC

(57) ABSTRACT

Provided herein are LILRB4-binding antibodies and methods of treating cancer by administering the LILRB4-binding antibodies alone or in combination with other therapies. Recombinant polypeptides comprising the CDRs of LILRB4-binding antibodies are also provided.

20 Claims, 25 Drawing Sheets

Specification includes a Sequence Listing.

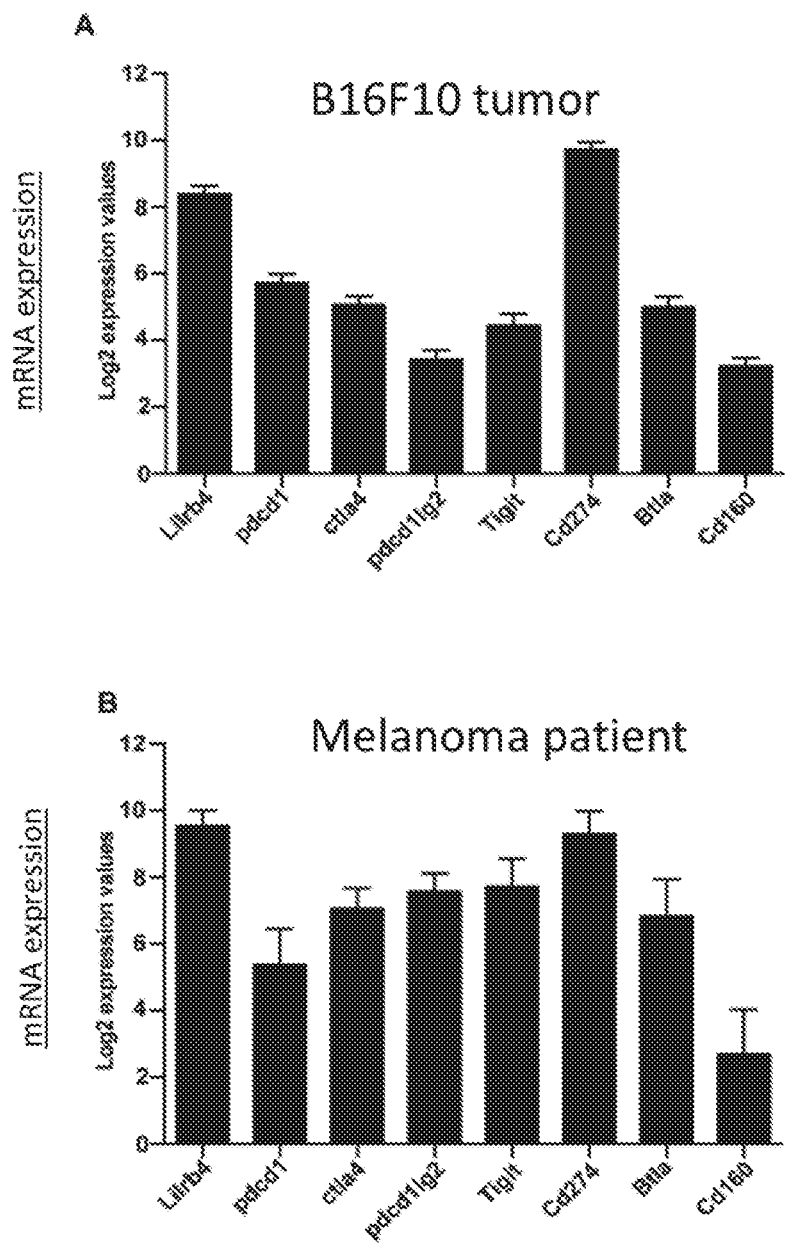
FIG. 1A-B

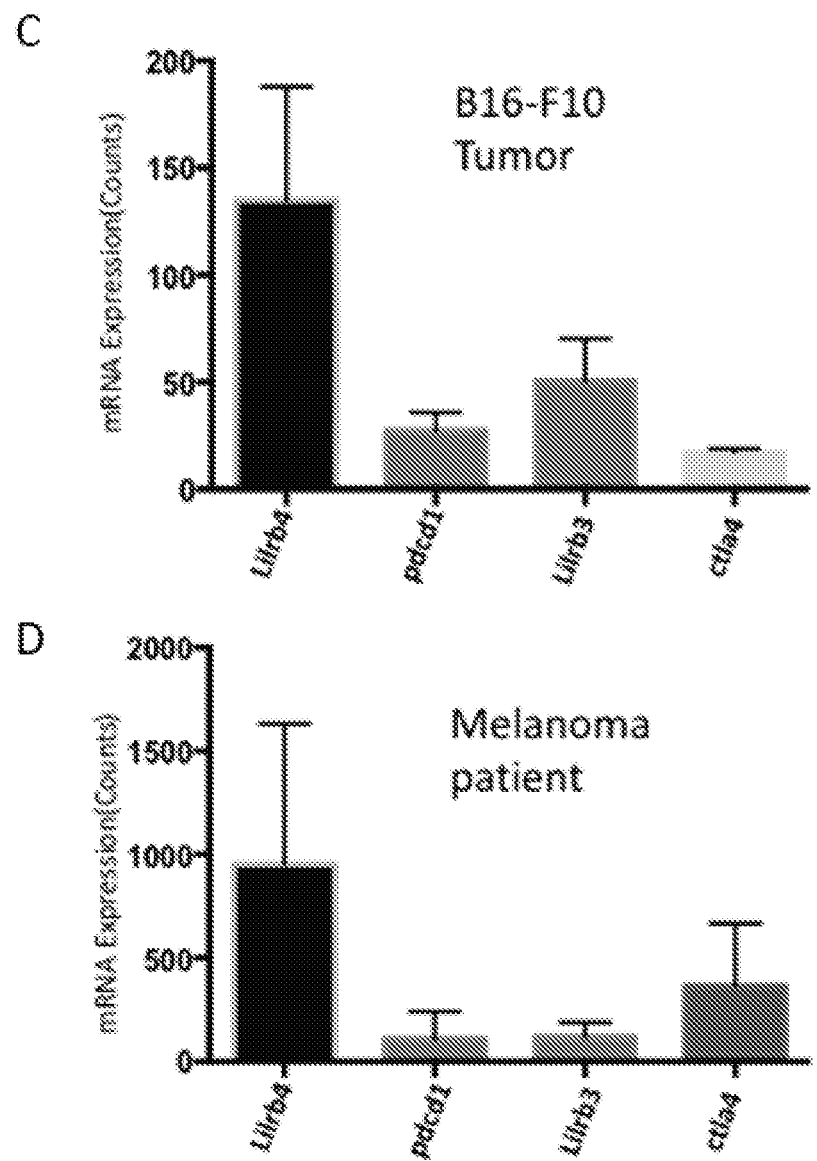
FIG. 1C-D

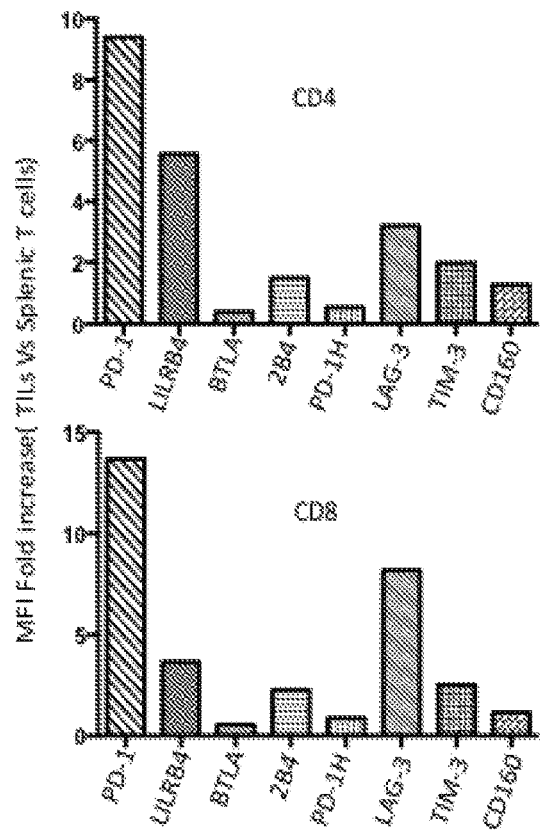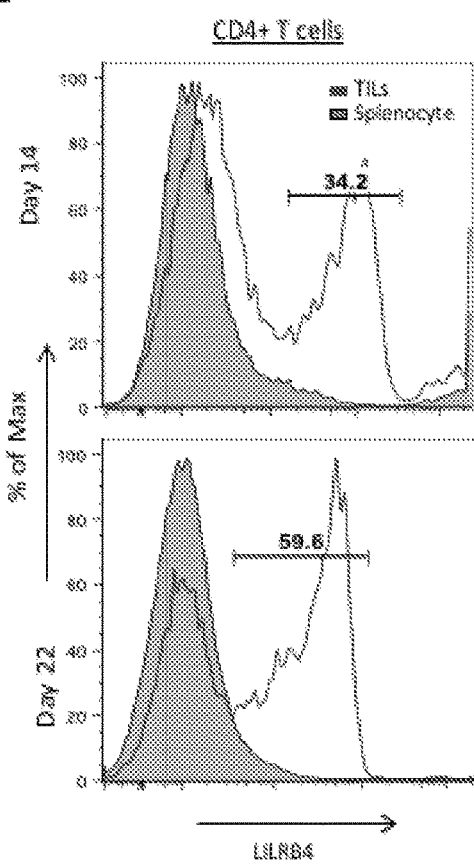
FIG. 2A-B

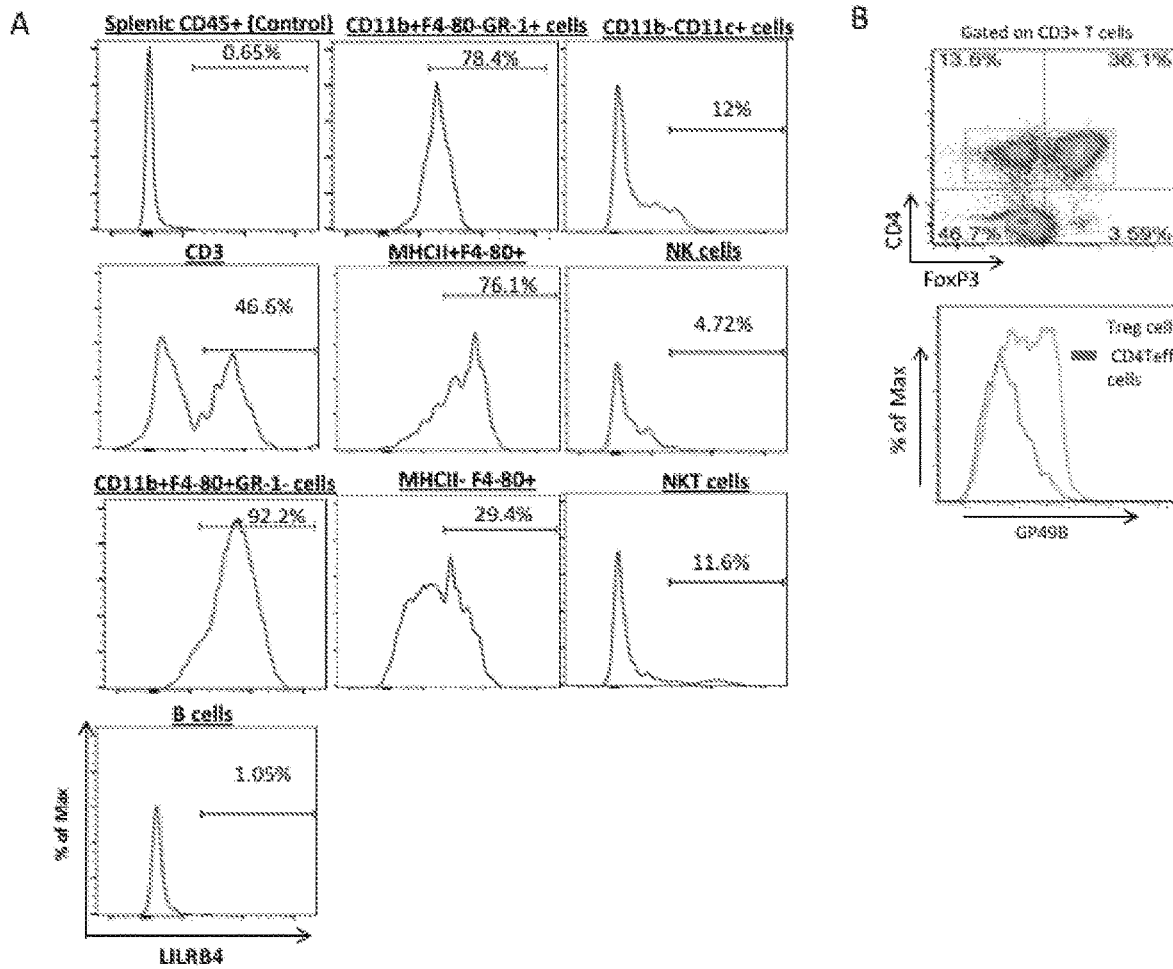
FIG. 3A-B

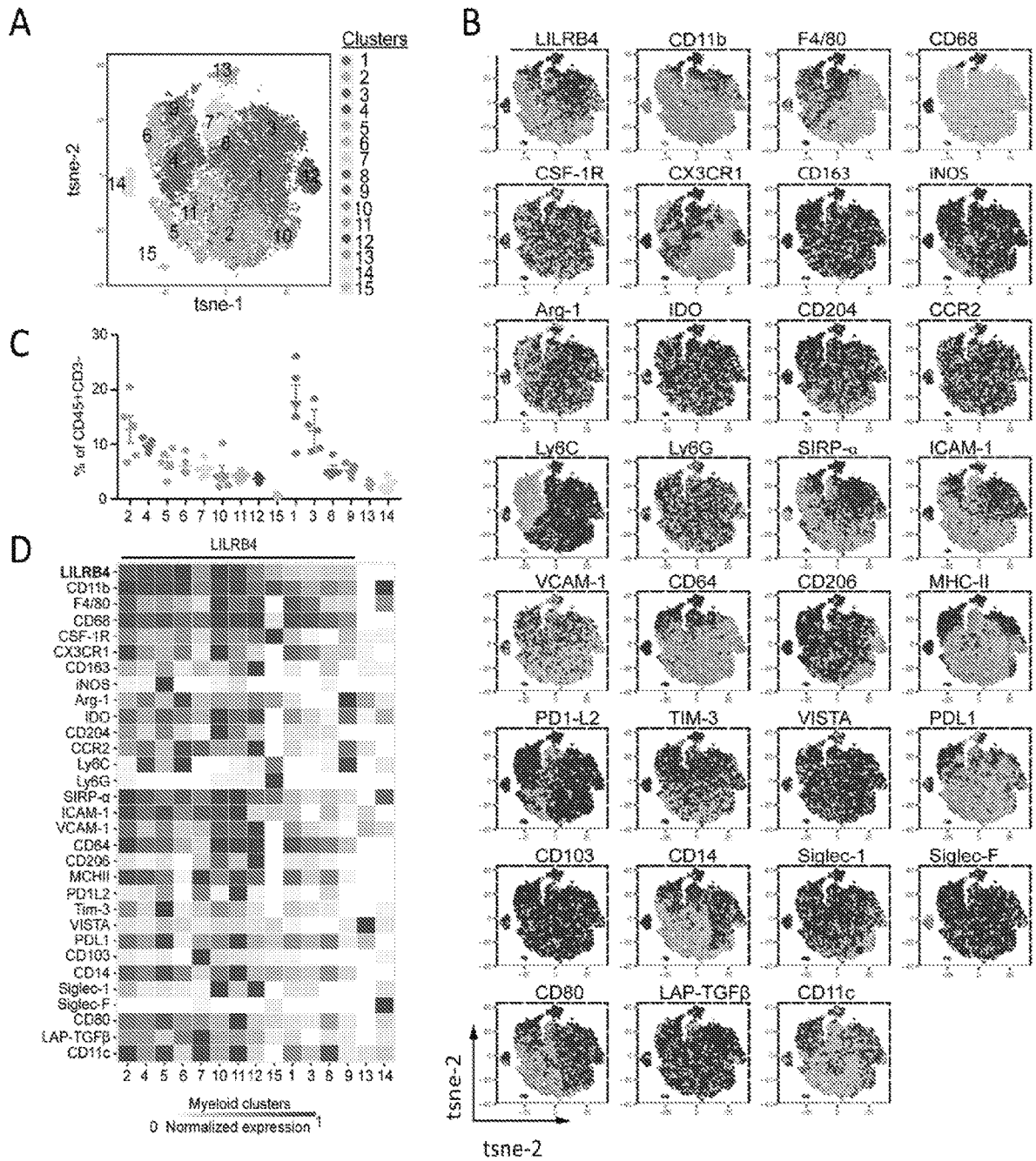
FIG. 4A-D

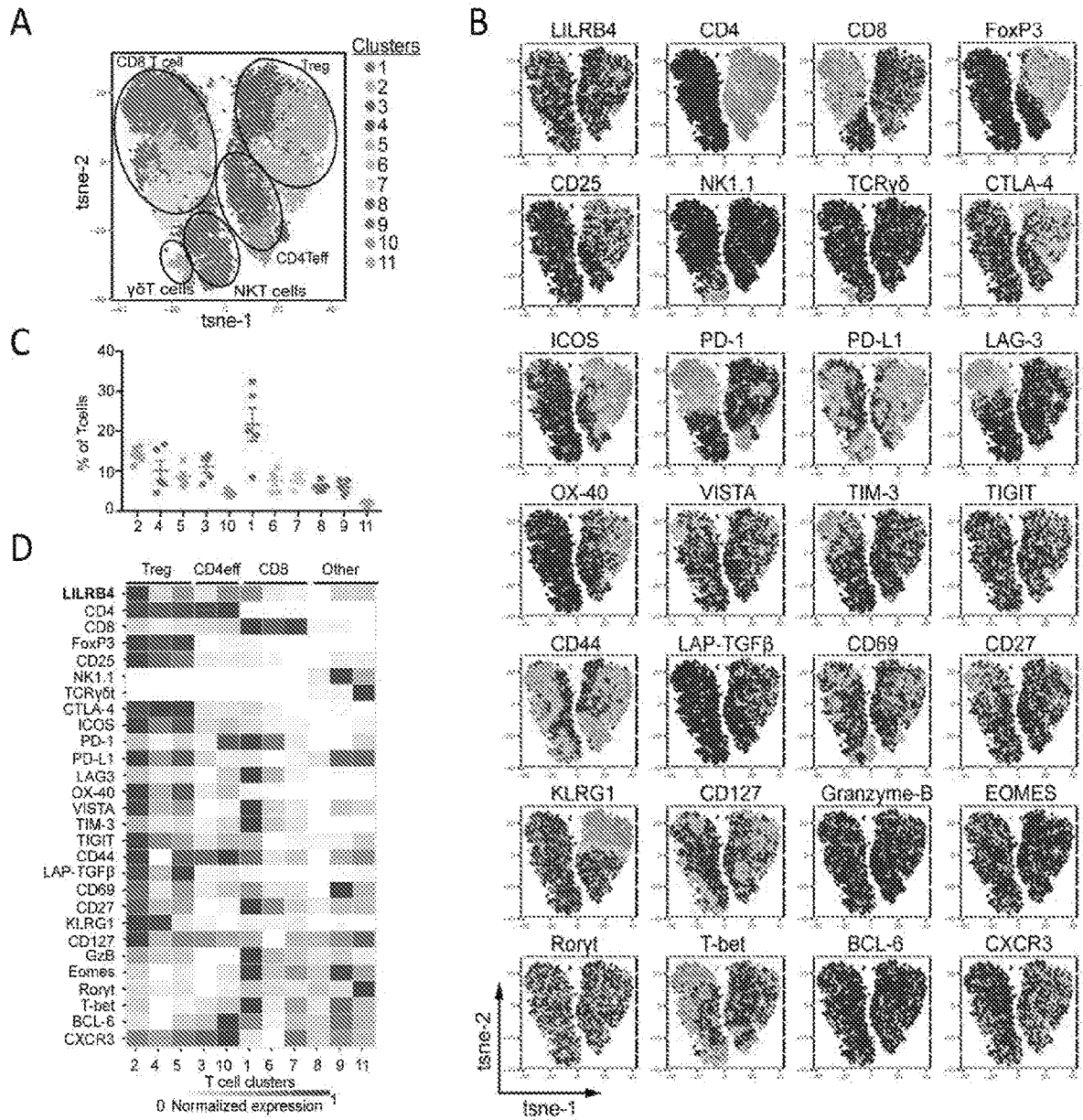
FIG. 5A-D

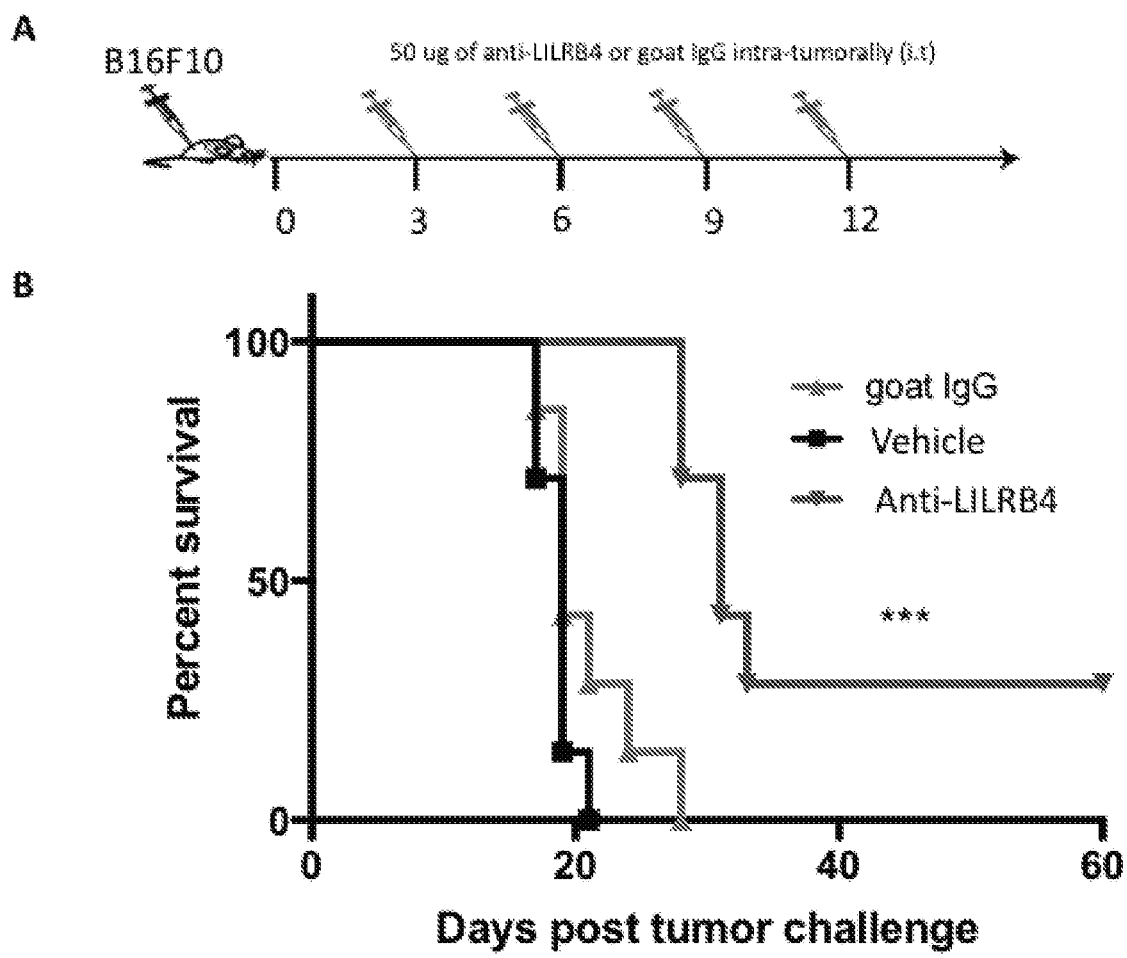
FIG. 6A-B

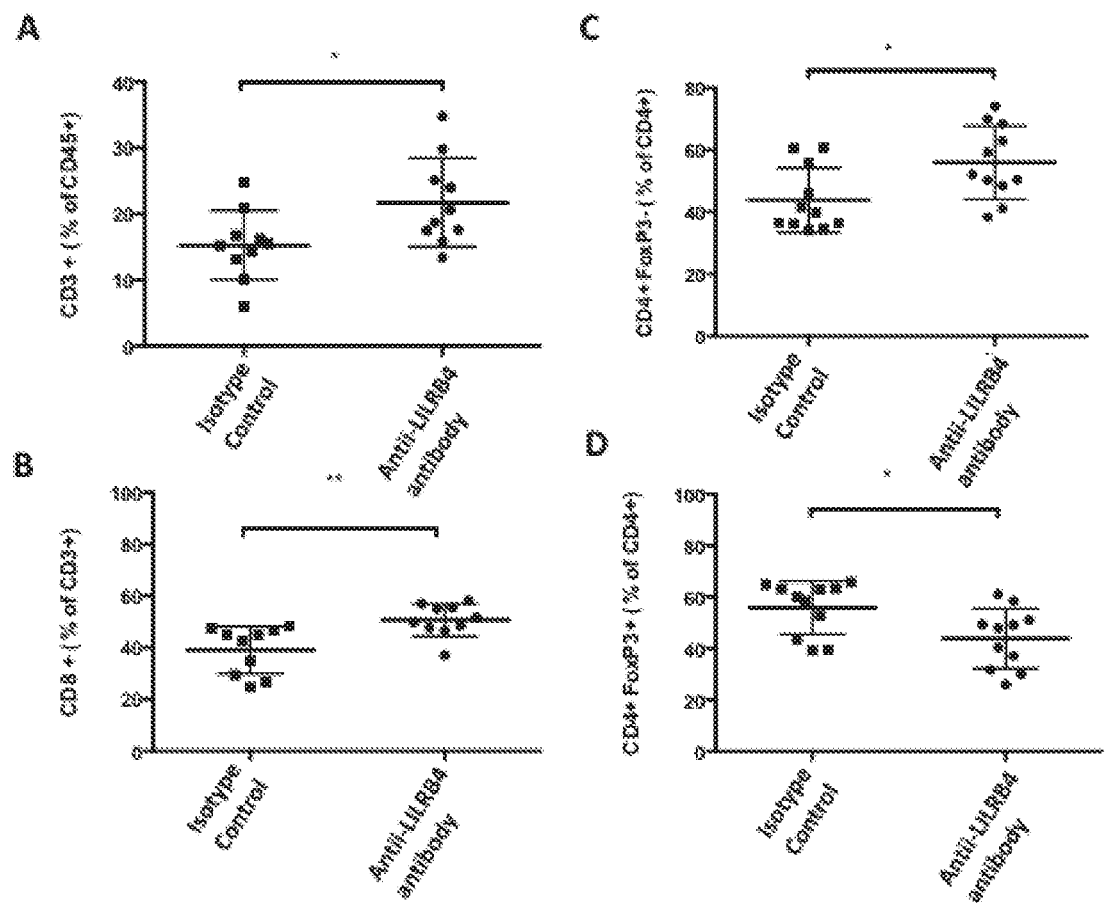
FIG. 7A-D

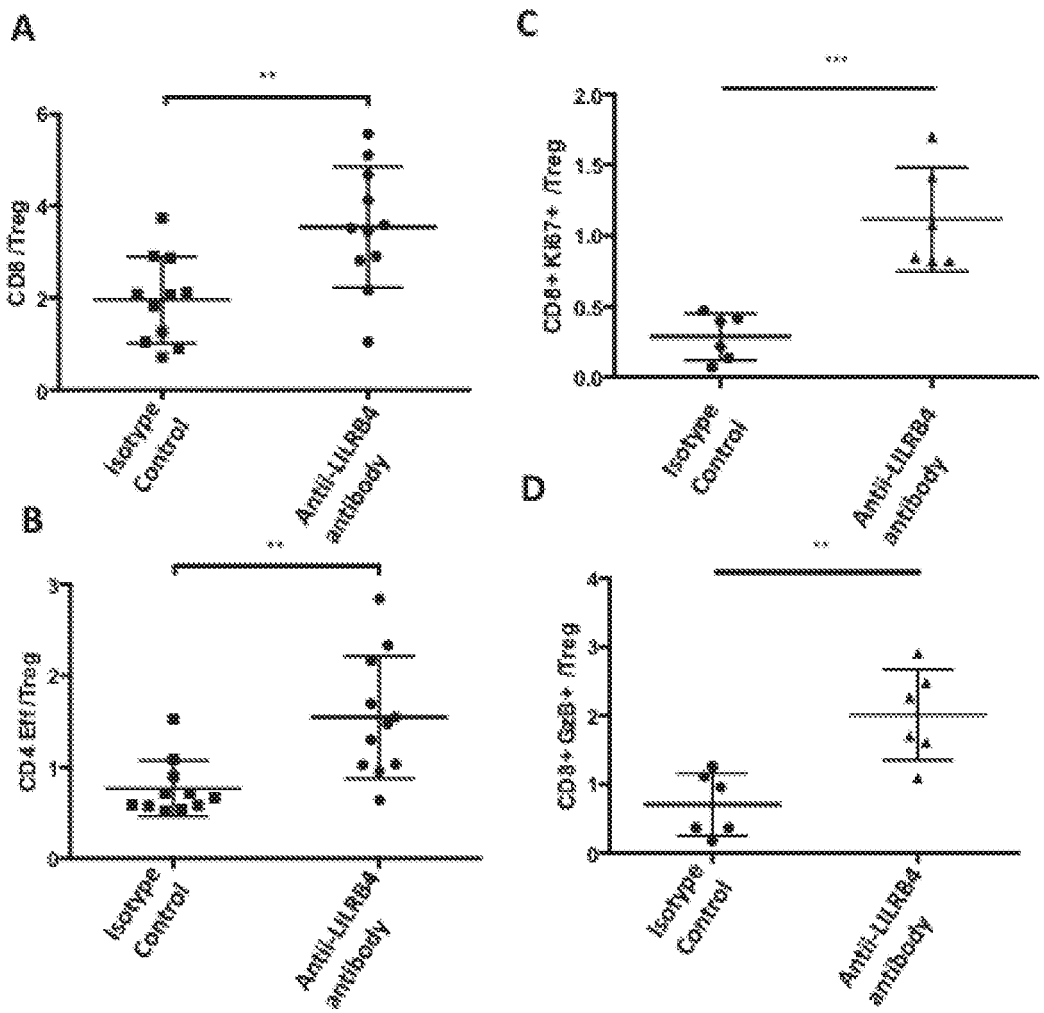
FIG. 8A-D

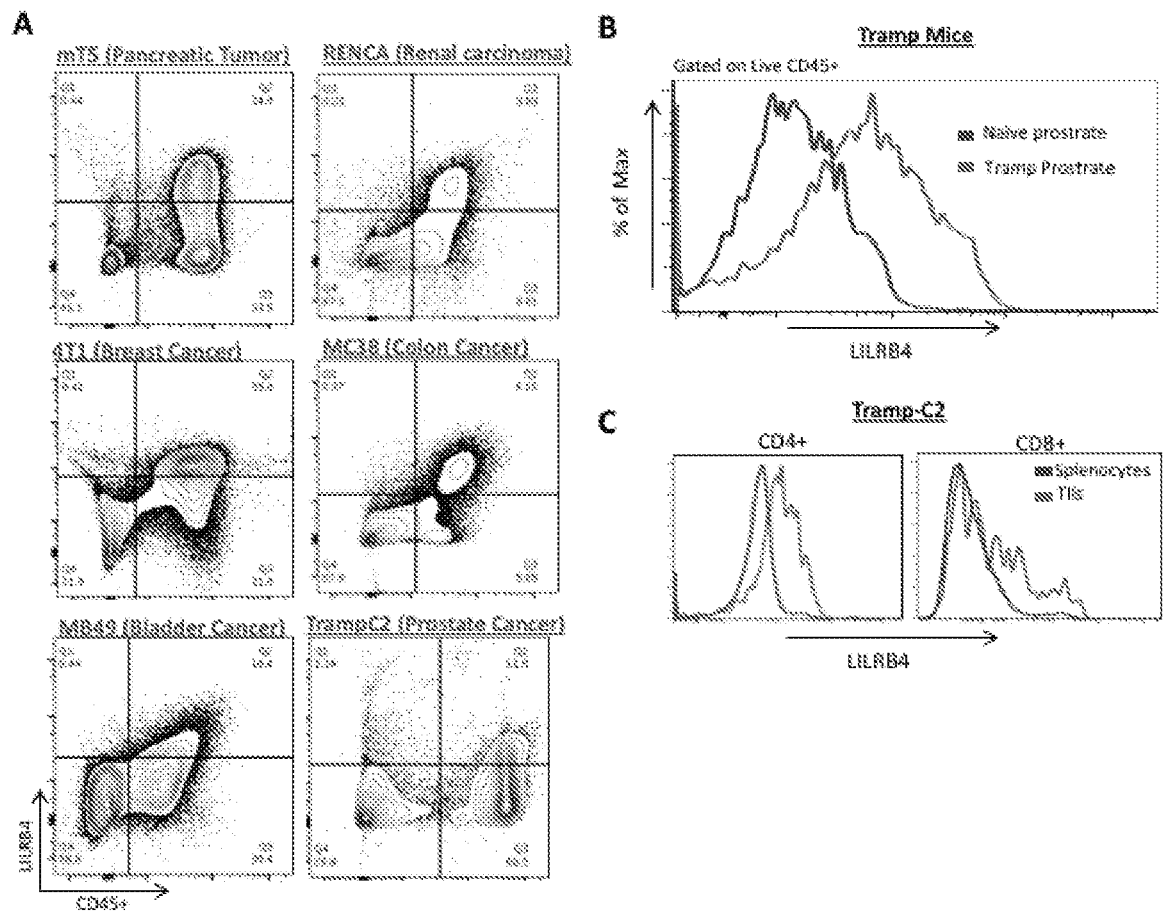
FIG. 9A-C

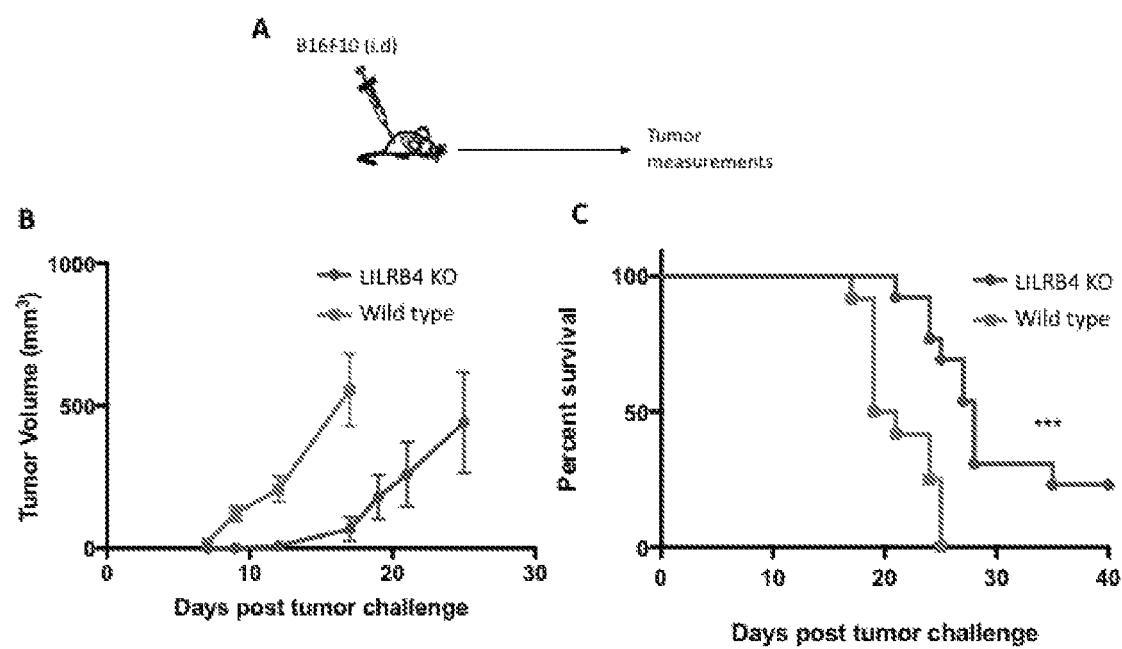
FIG. 10A-C

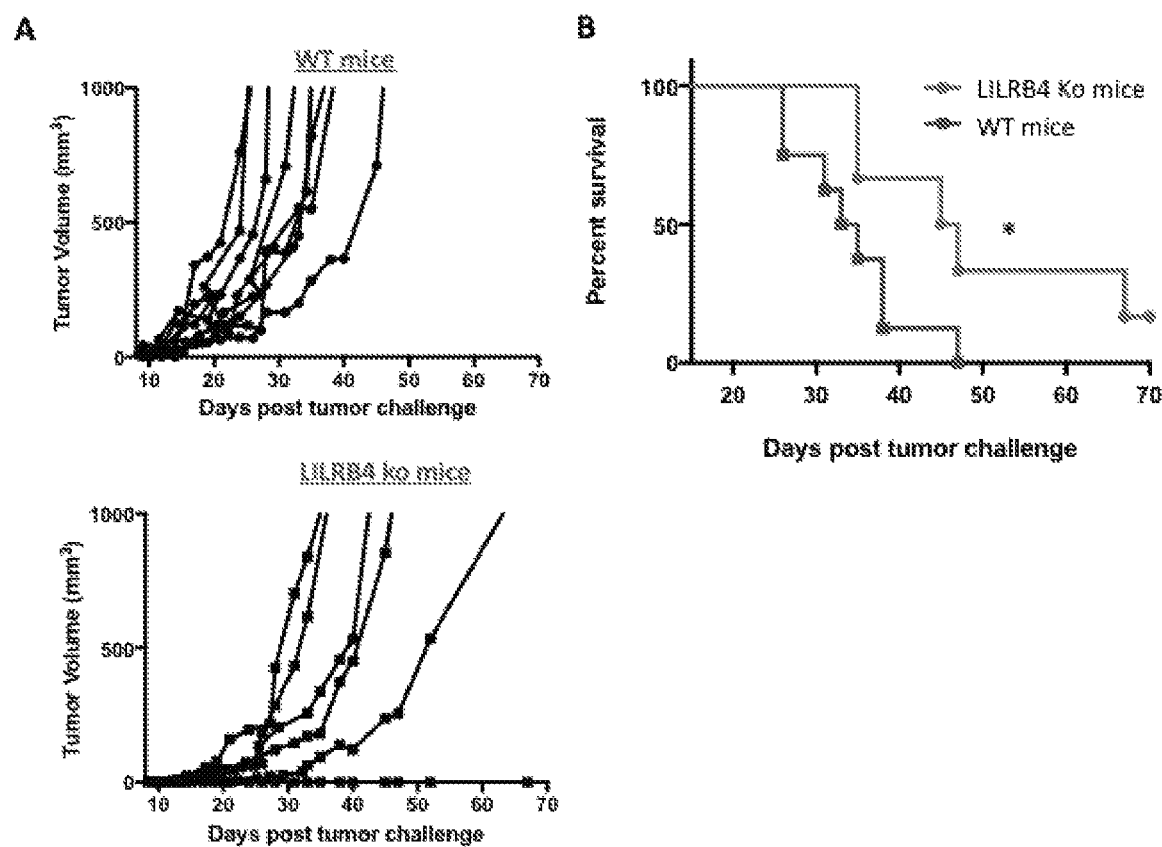
FIG. 11A-B

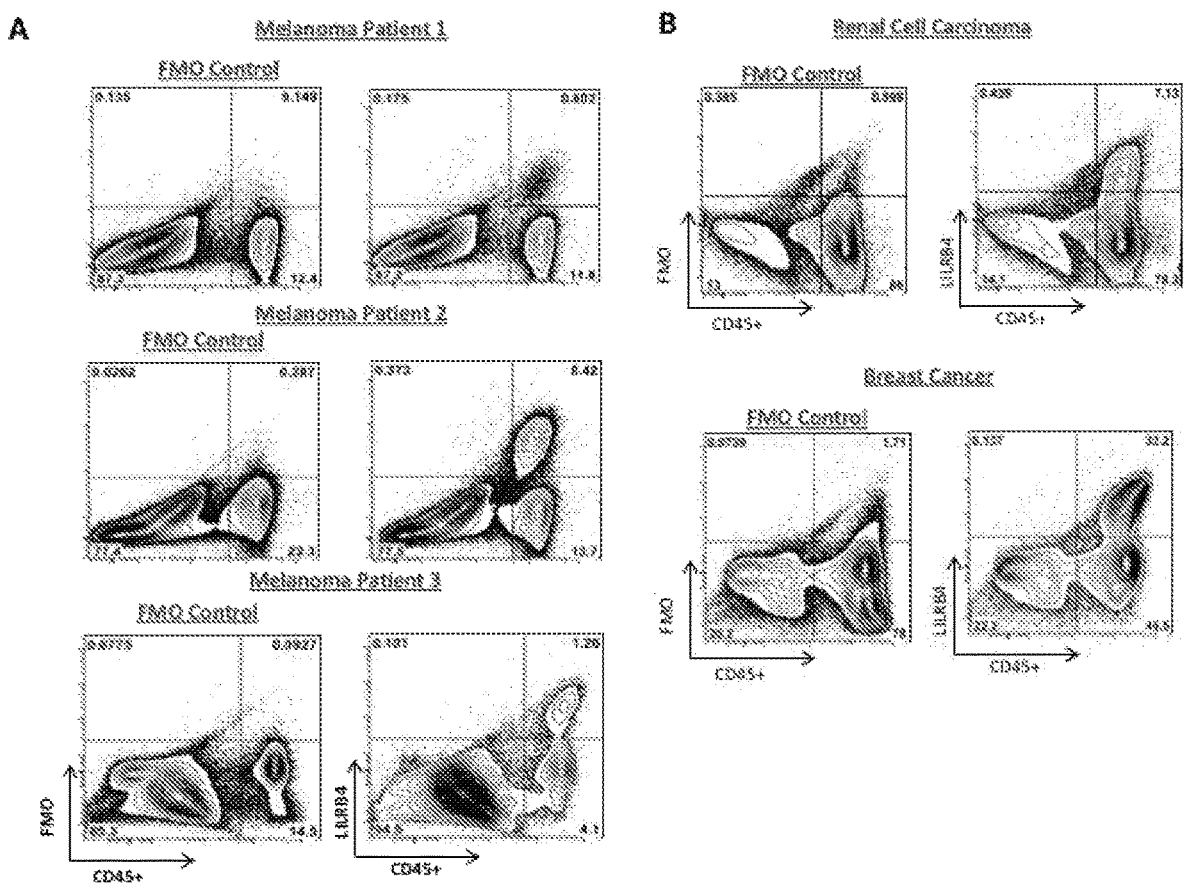
FIG. 17A-B

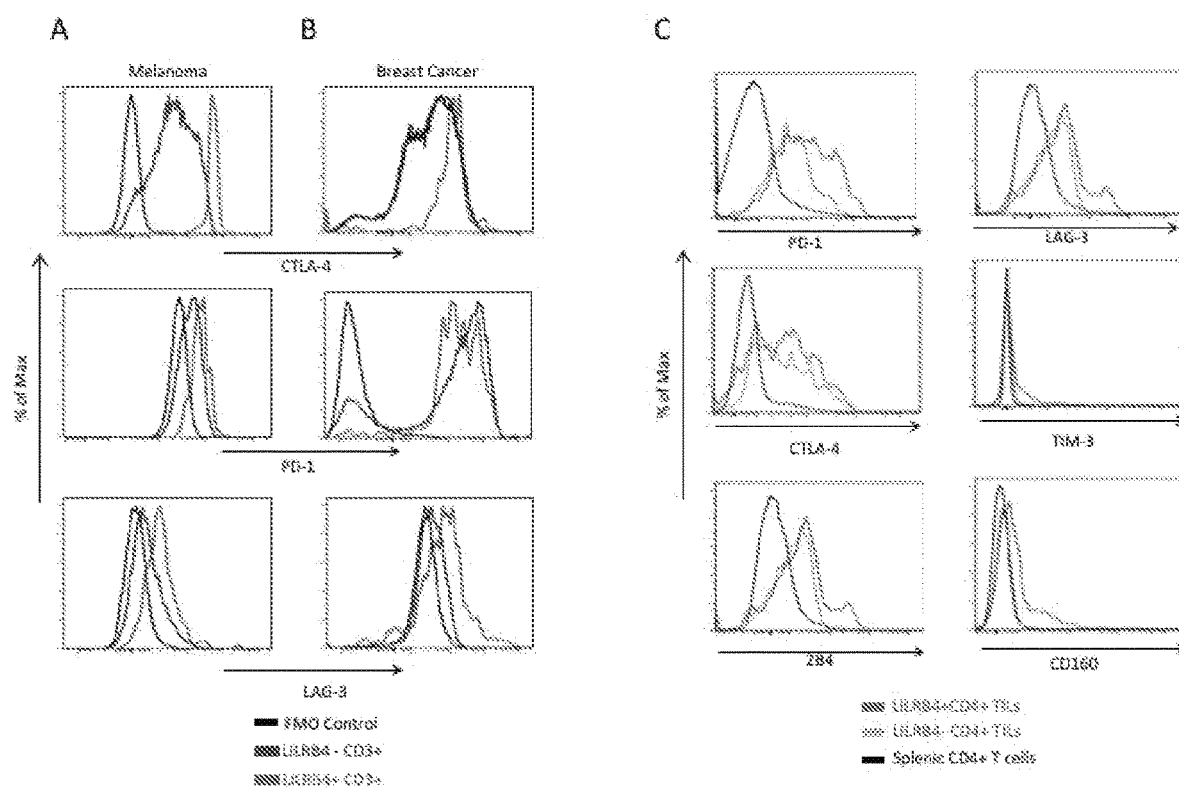
FIG. 18A-C

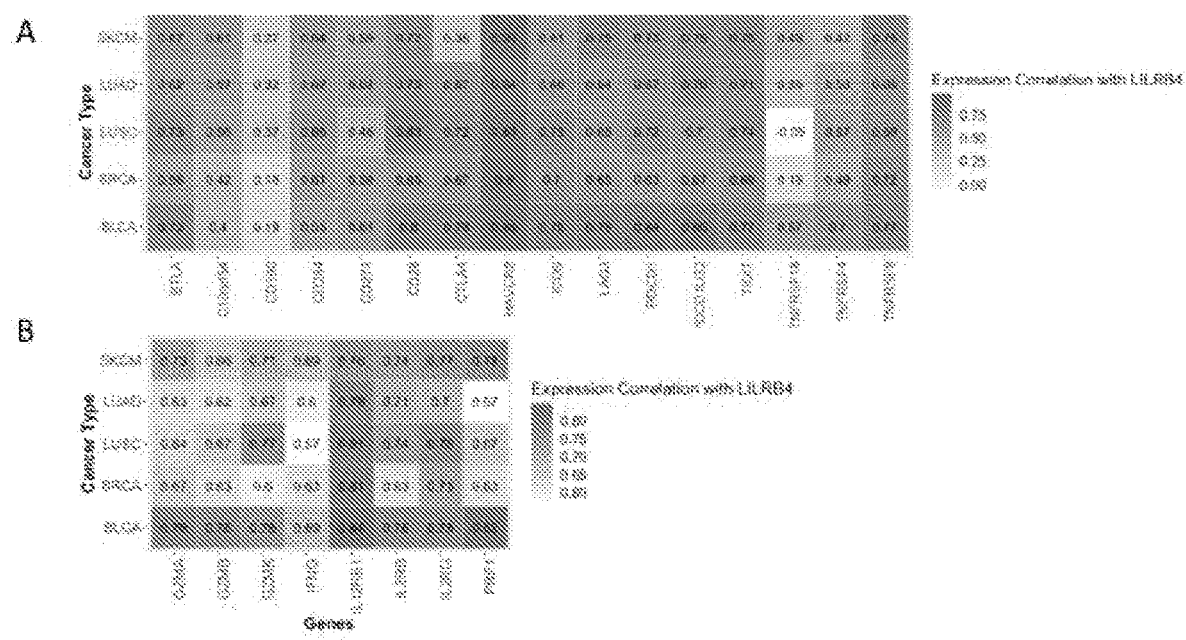
FIG. 20A-B

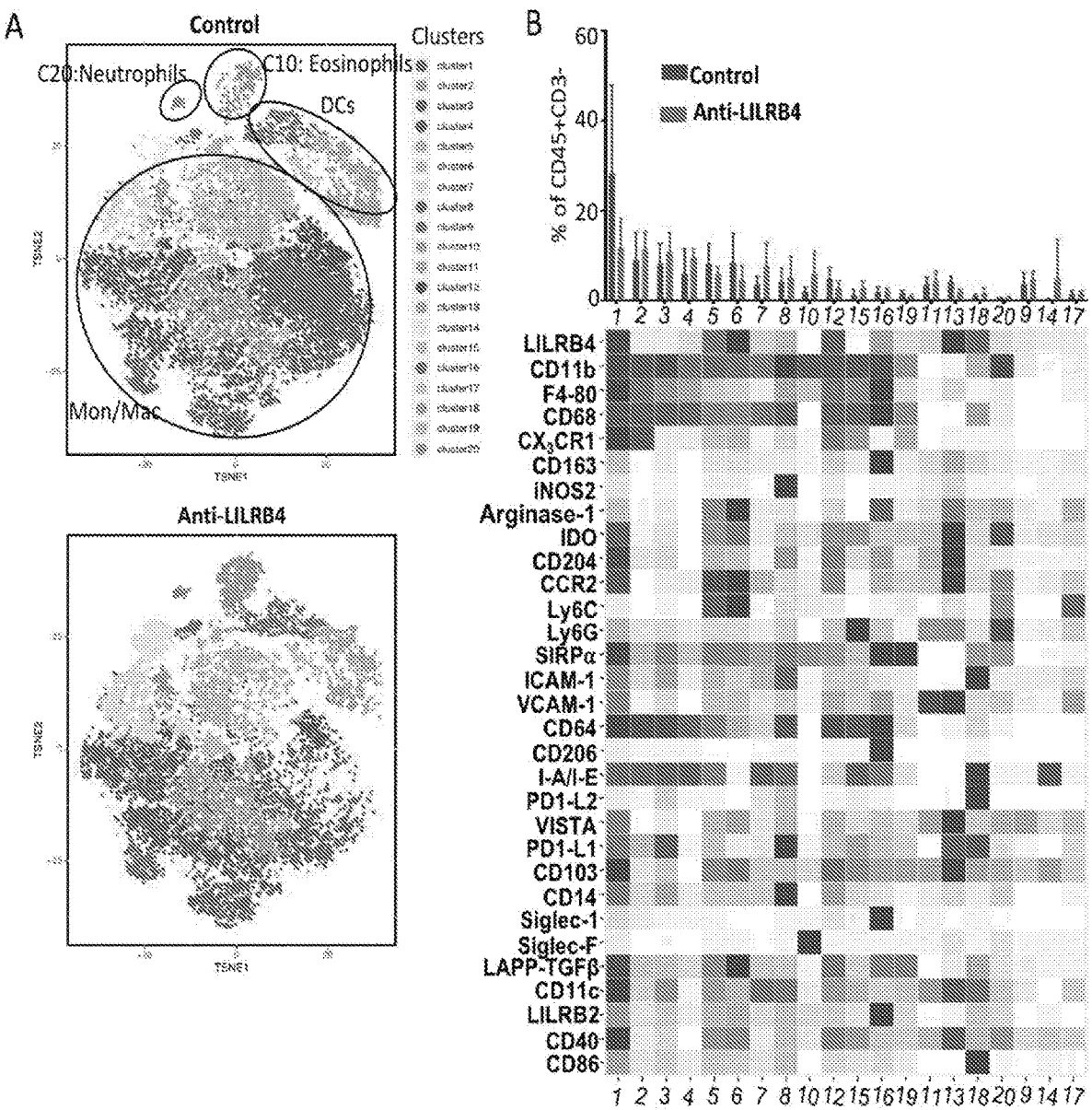
FIG. 22A-B

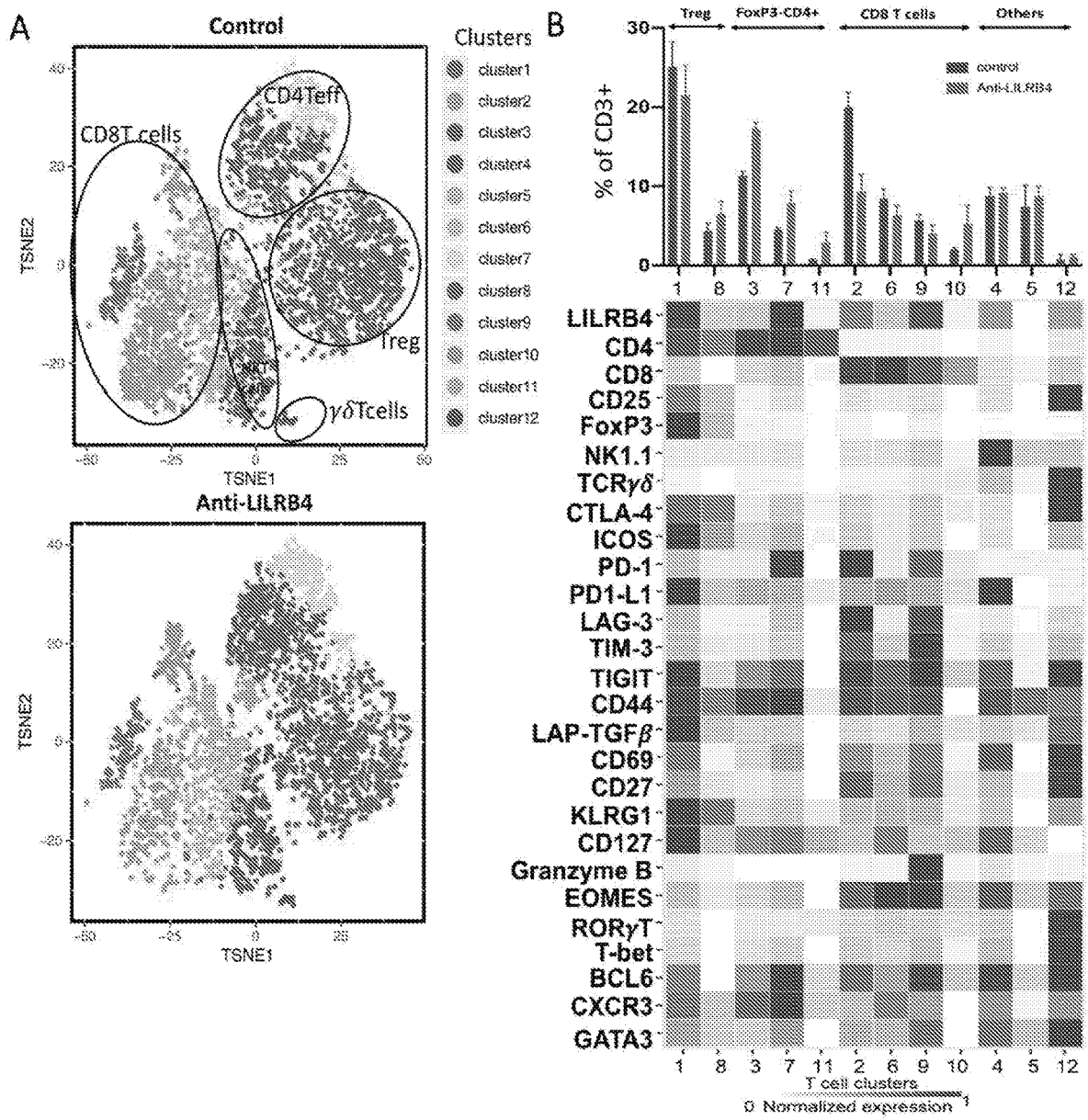
FIG. 23A-B

SEQUENCE LISTING

```
<160> NUMBER OF SEQ ID NOS: 15

<210> SEQ ID NO 1
<211> LENGTH: 8
<212> TYPE: PRT
<213> ORGANISM: Artificial sequence
<220> FEATURE:
<223> OTHER INFORMATION: Synthetic antibody

<400> SEQUENCE: 1

Gly Phe Met Phe Ser Ser Tyr Trp
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic antibody

<400> SEQUENCE: 2

Ile Asn Lys Asp Val Thr Thr Thr
1               5

<210> SEQ ID NO 3
<211> LENGTH: 13
<212> TYPE: PRT
<213> ORGANISM: Artificial sequence
<220> FEATURE:
<223> OTHER INFORMATION: Synthetic antibody
```

```
<400> SEQUENCE: 3

Val Arg Asn His Gly Ser Arg Tyr Ala Tyr Phe Asp Val
1               5                   10

<210> SEQ ID NO 4
<211> LENGTH: 7
<212> TYPE: PRT
<213> ORGANISM: Artificial sequence
<220> FEATURE:
<223> OTHER INFORMATION: Synthetic antibody

<400> SEQUENCE: 4

Thr Gln His Arg Thr Phe Tyr
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic antibody

<400> SEQUENCE: 5

Val Asn Ser Asp Gly Ser Gln
1               5

<210> SEQ ID NO 6
<211> LENGTH: 13
<212> TYPE: PRT
<213> ORGANISM: Artificial sequence
<220> FEATURE:
<223> OTHER INFORMATION: Synthetic antibody

<400> SEQUENCE: 6

Gly Val Asn Tyr Glu Ser Gly Lys Gln Tyr Gly Tyr Val
1               5                   10

<210> SEQ ID NO 7
<211> LENGTH: 9
<212> TYPE: PRT
<213> ORGANISM: Artificial sequence
<220> FEATURE:
<223> OTHER INFORMATION: Synthetic antibody

<400> SEQUENCE: 7

Asn Gly Ile Ser Val Gly Gly Lys Asn
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic antibody

<400> SEQUENCE: 8

Tyr Tyr Ser Asp Ser Asp Lys
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic antibody

<400> SEQUENCE: 9
```

```
Ser Ile Tyr Glu Ser Asn Thr Trp Val
1               5

<210> SEQ ID NO 10
<211> LENGTH: 120
<212> TYPE: PRT
<213> ORGANISM: Artificial sequence
<220> FEATURE:
<223> OTHER INFORMATION: Synthetic antibody

<400> SEQUENCE: 10

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Met Phe Ser Ser Tyr
                20                  25                  30

Trp Met Asn Trp Val Arg Gln Ala Pro Gly Lys Arg Leu Glu Trp Val
            35                  40                  45

Gly Asp Ile Asn Lys Asp Val Thr Thr Thr Asn Tyr Ser Pro Ser Val
        50                  55                  60

Lys Gly Arg Phe Thr Ile Ser Arg Asp Asn Ala Lys Ser Ile Leu Tyr
65                  70                  75                  80

Leu Gln Met Asn Ser Val Lys Ser Glu Asp Thr Ala Thr Tyr Tyr Cys
                85                  90                  95

Val Arg Asn His Gly Ser Arg Tyr Ala Tyr Phe Asp Val Trp Gly Gln
            100                 105                 110

Gly Ile Gln Val Thr Val Ser Ser
        115                 120

<210> SEQ ID NO 11
<211> LENGTH: 115
<212> TYPE: PRT
<213> ORGANISM: Artificial sequence
<220> FEATURE:
<223> OTHER INFORMATION: Synthetic antibody

<400> SEQUENCE: 11

Gln Pro Val Leu Thr Gln Ser Pro Ser Ala Ser Ala Ser Pro Gly Ala
1               5                   10                  15

Ser Val Arg Leu Thr Cys Thr Leu Ser Thr Gln His Arg Thr Phe Tyr
                20                  25                  30

Ile Glu Trp Tyr Gln Gln Tyr Pro Asp Lys Ala Pro Lys Tyr Val Met
            35                  40                  45

Lys Val Asn Ser Asp Gly Ser Gln Tyr Lys Gly Asp Gly Ile Pro Asp
        50                  55                  60

Arg Phe Ser Gly Ser Ser Ser Gly Ala His Arg Tyr Leu Thr Ile Ser
65                  70                  75                  80

Asn Ile Gln Ser Glu Asp Glu Ala Asp Tyr Ile Cys Gly Val Asn Tyr
                85                  90                  95

Glu Ser Gly Lys Gln Tyr Gly Tyr Val Phe Gly Ser Gly Thr Gln Val
            100                 105                 110

Thr Val Leu
        115

<210> SEQ ID NO 12
<211> LENGTH: 115
<212> TYPE: PRT
<213> ORGANISM: Artificial sequence
<220> FEATURE:
<223> OTHER INFORMATION: Synthetic antibody
```

<400> SEQUENCE: 12

Gln Ser Ile Leu Thr Gln Pro Pro Ser Ile Ser Glu Ser Leu Gly Ser
1               5                   10                  15

Thr Ala Arg Leu Thr Cys Thr Leu Asn Asn Gly Ile Ser Val Gly Gly
            20                  25                  30

Lys Asn Ile Tyr Trp Tyr Gln Gln Met Ala Gly Ser Val Pro Arg Leu
        35                  40                  45

Phe Leu Tyr Tyr Tyr Ser Asp Ser Asp Lys Glu Leu Gly Pro Gly Val
    50                  55                  60

Pro Asn Arg Asp Ser Gly Ser Lys Asp Thr Ser Lys Lys Ala Ala Asn
65                  70                  75                  80

Leu Gln Ile Ser Glu Leu Gln Val Glu Asp Glu Ala Val Cys Phe Cys
                85                  90                  95

Ser Ile Tyr Glu Ser Asn Thr Trp Val Phe Gly Ser Gly Thr Lys Val
            100                 105                 110

Thr Val Leu
        115

<210> SEQ ID NO 13
<211> LENGTH: 360
<212> TYPE: DNA
<213> ORGANISM: Artificial sequence
<220> FEATURE:
<223> OTHER INFORMATION: Synthetic antibody

<400> SEQUENCE: 13

```
gaagtgaagc tggtggagtc tggtggtggc ctggtgaaac tggagggtc cctgaaactc      60
tcctgtgctg cctctggatt catgttcagt agctactgga tgaactgggt ccgccaggct    120
cctggcaagc ggctggagtg ggttggagac attaataaag atgtcactac cacaaactat    180
tcaccatccg tgaagggccg cttcaccatc tctagagaca tgccaagag tattctgtac    240
ctgcaaatga acagtgtgaa gtctgaggac accgccactt attactgtgt tagaaaccac    300
ggtagccgct atgcttactt tgatgtctgg ggccagggga tccaggtcac cgtctcctca    360
```

<210> SEQ ID NO 14
<211> LENGTH: 346
<212> TYPE: DNA
<213> ORGANISM: Artificial sequence
<220> FEATURE:
<223> OTHER INFORMATION: Synthetic antibody

<400> SEQUENCE: 14

```
caacctgtgc tgactcagtc accctctgcc tctgcctccc cgggagcctc agtcagactc     60
acctgcacct tgagtactca gcacagaacc ttctacatag aatggtatca gcaatatcca    120
gacaaggctc ctaagtatgt gatgaaagtt aatagtgatg aagtcaata caaggtggat    180
gggatccctg atcgcttctc tggctccagt tctgggctc atcgctactt aacaatctcc    240
aacattcagt ctgaagatga agctgactac atctgtggtg ttaattatga agtggtaaa    300
caatatgggt atgtttttgg cagcggaacc aggtcaccg tcctag                   346
```

<210> SEQ ID NO 15
<211> LENGTH: 346
<212> TYPE: DNA
<213> ORGANISM: Artificial sequence
<220> FEATURE:
<223> OTHER INFORMATION: Synthetic antibody

```
<400> SEQUENCE: 15
cagtctatat tgacacaacc accctccatc tctgagtctc ttggatcaac agccagactc        60
acctgcaccc tgaataatgg catcagtgtt ggtggtaaaa atatttactg gtaccagcaa       120
atggcgggga gtgttcctcg tttgttcctg tactactact cagattcaga caaggagctg       180
gggcctggag tccccaacag agactctgga tccaaagata cctccaaaaa agctgcaaat       240
ttgcagatct ctgagctaca ggtggaggat gaggctgtgt gtttctgttc catctatgaa       300
agtaatactt gggtgttcgg ttcaggcacc aaagtgactg tcctag                     346
```

US 12,180,277 B2

LILRB4-BINDING ANTIBODY AND METHODS OF USE THEREOF

REFERENCE TO RELATED APPLICATIONS

This application is a national phase application under 35 U.S.C. § 371 of International Application No. PCT/US2020/020651, filed Mar. 2, 2020, which claims the benefit of U.S. Provisional Patent Application No. 62/812,700, filed Mar. 1, 2019, the entirety of which is incorporated herein by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Mar. 2, 2020, is named UTFCP1392WO_ST25.txt and is 7 kilobytes in size.

BACKGROUND

1. Field

The present invention relates generally to the fields of immunology, oncology and medicine. More particularly, it concerns anti-LILRB4 antibodies and methods of use thereof.

2. Description of Related Art

Current immunotherapy drugs have been shown to be effective in treating some cancers but still complete cure of many other cancers remain a challenge. Also, the fact that a vast range of co-receptors/co-inhibitors are expressed on T cells and have not been studied in tumor context, has led to a search for new targets. LILRBs may inhibit activities of a number of immune cell types facilitating tumor immune escape. LILRB4 is a member of Ig-like receptor family B (LILRB) and has extracellular Ig-like domains that bind ligands and Intracellular ITIMs. There are 5 members in this family from LILRB1-LILRB5 and most LILRBs are primate and human specific. There are two mouse orthologues: paired immunoglobulin-like receptor B (PirB) for LILRB2/3 and gp49B for LILRB4. Integrin $\alpha_v\beta_3$ is the only known ligand of LILRB4 and is known to inhibit mast cell activation when interacts which LILRB4 (gp4913) by recruitment of SHP-1. LILRB4 is expressed on monocytes, macrophages, mast cells, B cells, NK cells, T cells and dendritic cells. LILRB4 expression on T cells has been shown to regulate T cell function in acute viral model. Expression of LILRB4 on myeloid population can also inhibit T cell activation through indirect mechanism. Likewise, LILRB4 is a specific marker for monocytic AML including refractory and relapsed disease.

SUMMARY

In certain embodiments, the present disclosure provides LILRB4-binding antibodies. In some aspects, the LILRB4-binding antibody is an isolated monoclonal antibody, wherein the antibody specifically binds to LILRB4 and comprises (a) a first $V_H$ CDR of SEQ ID NO: 1 (GFMFSSYW); (b) a second $V_H$ CDR of SEQ ID NO: 2 (INKDVITT); (c) a third $V_H$ CDR of SEQ ID NO: 3 (VRNIIGSRYAYFDV); (d) a first $V_L$ CDR of SEQ ID NO: 4 (TQFIRTFY); (e) a second $V_L$ CDR of SEQ ID NO: 5 (VNSDGSQ); and (f) a third $V_L$ CDR of SEQ ID NO: 6 (GVNYESGKQYGYV). In certain aspects, the antibody comprises (a) a first $V_H$ CDR of SEQ II) NO: 1 (GFMFSSYW); (b) a second $V_H$ CDR of SEQ ID NO: 2 (INKDVTTT); (c) a third $V_H$ CDR of SEQ ID NO: 3 (VRNHGSRYAYFDV); (d) a first $V_L$ CDR of SEQ ID NO: 7 (NGISVGGKN); (e) a second $V_L$ CDR of SEQ ID NO: 8 (YYSDSDK); and (f) a third $V_L$ CDR of SEQ ID NO: 9 (SIYESNTWV).

In certain aspects, the antibody comprises a first pair of VH and VL domains comprising (I) (a) a first $V_H$ CDR of SEQ ID NO: 1 (GFMFSSYW); (b) a second $V_H$ CDR of SEQ ID NO: 2 (LNKDVTTT); (c) a third $V_H$ CDR of SEQ ID NO: 3 (VRNHGSRYAYFDV); (d) a first $V_L$ CDR of SEQ ID NO: 4 (TQHRIFY); (e) a second $V_L$ CDR of SEQ ID NO: 5 (VNSDGSQ); and (f) a third $V_L$ CDR of SEQ ID NO: 6 (GYNYESGKQYGYV); and a second pair or VH and VL domains comprising (a) a first $V_H$ CDR of SEQ ID NO: 1 (GFMFSSYW); (b) a second $V_H$ CDR of SEQ II) NO: 2 (INKDVTTT); (c) a third $V_H$ CDR of SEQ ID NO: 3 (VRNHGSRYAYFDV); (d) a first $V_L$ CDR of SEQ ID NO: 4 (TQHRTFY); (e) a second $V_L$ CDR of SEQ II) NO: 5 (VNSDGSQ); and (f) a third $V_L$ CDR of SEQ ID NO: 6 (GVNYESGKQYGYV). In some aspects, the antibody comprises a first pair of VH and VL domains comprising (a) a first $V_H$ CDR of SEQ ID NO: 1 (GFMFSSYW); (b) a second $V_H$ CDR of SEQ ID NO: 2 (LNKDVTTT); (c) a third $V_H$ CDR of SEQ ID NO: 3 (VRNIIGSRYAYFDV); (d) a first $V_L$ CDR of SEQ ID NO: 7 (NGISVGGKN); (e) a second $V_L$ CDR of SEQ ID NO: 8 (YYSDSDK); and (f) a third $V_L$ CDR of SEQ ID NO: 9 (SIYESNTWV); and a second pair or VH and VL domains comprising: (a) a first $V_H$ CDR of SEQ ID NO: 1 (GFMFSSYW); (h) a second $V_H$ CDR of SEQ ID NO: 2 (INKDVTTT); (c) a third. VIA CDR of SEQ ID NO: 3 (VRNHGSRYAYFDV); (d) a first $V_L$ CDR of SEQ ID NO: 7 (NGISVGGKN); (e) a second $V_L$ CDR of SEQ ID NO: 8 (YYSDSDK); and (f) a third $V_L$ CDR of SEQ ID NO: 9 (SIYESNTWV).

In some aspects, the antibody comprises a first pair of VH and VL domains comprising (I) (a) a first $V_H$ CDR of SEQ ID NO: 1 (GFMFSSYW); (b) a second $V_H$ CDR of SEQ ID NO: 2 (INKDVTTT); (c) a third $V_H$ CDR of SEQ ID NO: 3 (VRNHGSRYAYFDV); (d) a first $V_L$ CDR of SEQ ID NO: 4 (TQHRTFY); (e) a second $V_L$ CDR of SEQ ID NO: 5 (VNSDGSQ); and (f) a third $V_L$ CDR of SEQ ID NO: 6 (GVNYESGKQYGYV); and a second pair or VH and VL domains comprising (II) (a) a first $V_H$ CDR of SEQ ID NO: 1 (GFMFSSYW); (b) a second $V_H$ CDR of SEQ ID NO: 2 (INKDVTTT); (c) a third $V_H$ CDR of SEQ ID NO: 3 (VRNHGSRYAYFDV); (d) a first $V_L$ CDR of SEQ ID NO: 7 (NGISVGGKN); (e) a second $V_L$ CDR of SEQ ID NO: 8 (YYSDSDK); and (f) a third $V_L$ CDR of SEQ ID NO: 9 (SIYESNTWV).

In particular aspects, the antibody comprises a $V_H$ domain at least about 80% (e.g., 85%, 86%, 87%, 88%, 89%, 90%, 91%, 92%, 93%, 94%, 95%, 96%, 97%, 98%, or 99%) identical to the $V_H$ domain of SEQ ID NO: 10 and a $V_L$ domain at least about 80% (e.g., 85%, 86%, 87%, 88%, 89%, 90%, 91%, 92%, 93%, 94%, 95%, 96%, 97%, 98%, or 99%) identical to the $V_L$ domain of SEQ ID NO: 11. In some aspects, the antibody comprises a $V_H$ domain identical to the $V_H$ domain of SEQ ID NO: 10 and a $V_L$ domain identical to the $V_L$ domain of SEQ ID NO: 11. In specific aspects, the antibody comprises a $V_H$ domain at least about 80% (e.g., 85%, 86%, 87%, 88%, 89%, 90%, 91%, 92%, 93%, 94%, 95%, 96%, 97%, 98%, or 99%) identical to the $V_H$ domain of SEQ ID NO: 10 and a $V_L$ domain at least about 80% (e.g., 85%, 86%, 87%, 88%, 89%, 90%, 91%, 92%, 93%, 94%, 95%, 96%, 97%, 98%, or 99%) identical to the $V_L$ domain of SEQ ID NO: 12. In particular aspects, the antibody comprises a $V_H$ domain identical to the $V_H$ domain of SEQ ID NO: 10 and a $V_L$ domain identical to the $V_L$ domain of SEQ ID NO: 12.

In particular aspects, the antibody comprises a $V_H$ domain at least about 80% (e.g., 85%, 86%, 87%, 88%, 89%, 90%, 91%, 92%, 93%, 94%, 95%, 96%, 97%, 98%, or 99%) identical to the $V_H$ domain encoded by the sequence of SEQ ID NO: 13 and a $V_L$ domain at least about 80% (e.g., 85%, 86%, 87%, 88%, 89%, 90%, 91%, 92%, 93%, 94%, 95%, 96%, 97%, 98%, or 99%) identical to the $V_L$ domain encoded by the sequence of SEQ ID NO: 14. In some aspects, the antibody comprises a $V_H$ domain identical to the $V_H$ domain encoded by the sequence of SEQ ID NO: 13 and a $V_L$ domain identical to the $V_L$ domain encoded by the sequence of SEQ ID NO: 14. In specific aspects, the antibody comprises a $V_H$ domain at least about 80% (e.g., 85%, 86%, 87%, 88%, 89%, 90%, 91%, 92%, 93%, 94%, 95%, 96%, 97%, 98%, or 99%) identical to the $V_H$ domain encoded by the sequence of SEQ ID NO: 13 and a $V_L$ domain at least about 80% (e.g., 85%, 86%, 87%, 88%, 89%, 90%, 91%, 92%, 93%, 94%, 95%, 96%, 97%, 98%, or 99%) identical to the $V_L$ domain encoded by the sequence of SEQ ID NO: 15. In particular aspects, the antibody comprises a $V_H$ domain identical to the $V_H$ domain encoded by the sequence of SEQ ID NO: 13 and a $V_L$ domain identical to the $V_L$ domain encoded by the sequence of SEQ ID NO: 15.

In certain aspects, the antibody is recombinant. The antibody may be an IgG, IgM, IgA or an antigen binding fragment thereof. The antibody may be a Fab', a F(ab')2, a monovalent scFv, a bivalent scFv, or a single domain antibody. In certain aspects, the antibody is a human, humanized antibody or de-immunized antibody. The antibody may be conjugated to an imaging agent, a chemotherapeutic agent, a toxin or a radionuclide. A further embodiment provides a composition comprising a LILRB4-binding antibody of the embodiments in a pharmaceutically acceptable carrier.

Also provided herein is an isolated polynucleotide molecule comprising a nucleic acid sequence encoding a LILRB4-binding antibody of the embodiments. In particular aspects, the polynucleotide comprises a sequence at least about 80% (e.g., 85%, 86%, 87%, 88%, 89%, 90%, 91%, 92%, 93%, 94%, 95%, 96%, 97%, 98%, or 99%) identical to SEQ ID NO: 13 and a sequence at least about 80% (e.g., 85%, 86%, 87%, 88%, 89%, 90%, 91%, 92%, 93%, 94%, 95%, 96%, 97%, 98%, or 99%) identical to SEQ ID NO: 14. In some aspects, the polynucleotide comprises a sequence identical to SEQ ID NO: 13 and a sequence identical to SEQ ID NO: 14. In specific aspects, the polynucleotide comprises a sequence at least about 80% (e.g., 85%, 86%, 87%, 88%, 89%, 90%, 91%, 92%, 93%, 94%, 95%, 96%, 97%, 98%, or 99%) identical to SEQ ID NO: 13 and a sequence at least about 80% (e.g., 85%, 86%, 87%, 88%, 89%, 90%, 91%, 92%, 93%, 94%, 95%, 96%, 97%, 98%, or 99%) identical to SEQ ID NO: 15. In particular aspects, the polynucleotide comprises a sequence identical to SEQ ID NO: 13 and a sequence identical to SEQ ID NO: 15.

In another embodiment, there is provided a recombinant polypeptide comprising an antibody $V_H$ domain comprising CDRs 1-3 of the $V_H$ domain of SEQ ID NOs: 1, 2, and 3 and (I) CDRs 1-3 of the $V_L$ domain of SEQ ID NOs: 4, 5, and 6; or (II) CDRs 1-3 of the $V_L$ domain of SEQ ID NOs: 7, 8, and 9. Further provided herein is an isolated polynucleotide molecule comprising a nucleic acid sequence encoding a polypeptide of the embodiments.

A further embodiment provides a host cell comprising one or more polynucleotide molecule(s) encoding an antibody of the embodiments or a recombinant polypeptide of the embodiments. In some aspects, the host cell is a mammalian cell, a yeast cell, a bacterial cell, a ciliate cell or an insect cell.

Further provided herein is a pharmaceutical composition comprising a LILRB4-binding antibody of the embodiments and a pharmaceutical carrier. Also provided herein is a composition comprising an effective amount of a LILRB4-binding antibody of the embodiments for the treatment of cancer in a subject.

In another embodiment, there is provided the use of a composition comprising an effective amount of a LILRB4-binding antibody of the embodiments for the treatment of cancer in a subject.

Further provided herein is a method for treating cancer in a subject comprising administering an effective amount of a LILRB4-binding antibody of the embodiments to the subject. In some aspects, the cancer is leukemia, breast cancer, melanoma, prostate cancer, or pancreatic cancer.

In some aspects, the antibody is administered intravenously, intradermally, intratumorally, intramuscularly, intraperitoneally, subcutaneously, or locally. In particular aspects, the antibody is administered intravenously. In certain aspects, the antibody is in a pharmaceutically acceptable composition. In some aspects, the antibody is administered systemically. In additional aspects, the method further comprises administering at least a second anticancer therapy to the subject. In some aspects, the second anticancer therapy is a surgical therapy, chemotherapy, radiation therapy, cryotherapy, hormonal therapy, immunotherapy or cytokine therapy.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-D show nano string analysis of expression of Lilrb4 in B16/F10 tumor model and melanoma patients. (A) and (C) Mice were challenged with B16/F10 tumors. Tumors were dissected when tumor grows to a 1000 $mm^3$, digested and RNA was extracted for nanostring assay and analysis. (B) and (D) Total RNA was isolated from tumors of baseline melanoma patients for nanostring assay and analysis.

FIG. 2A-B shows LILRB4 expression on TILs relative to splenic T cells. Mice were challenged with B16/F10 tumors and when tumor grows to 1000 $mm^3$, mice were sacrificed and tumors were isolated. Tumor-infiltrating cells (TILs) and splenic cells (from same mice) were isolated and stained with flow antibodies and ran in flow cytometer. (A) Shows the mean fluorescence intensity (MFI) fold increase in various inhibitory receptors' expression including LILRB4 on tumor-infiltrating CD4 T cells and CD8 T cells compared to splenic CD4 and CD8 T cells. (B) Expression of LILRB4 on Tumor-infiltrating CD4 T cells compared to splenic CD4 T cells.

FIG. 3A-B shows LILRB4 expression on various cell types in tumor. Mice were challenged with B16/F10 tumor and when tumor grows to 1000 mm$^3$, mice were sacrificed and tumors were isolated. Tumor-infiltrating cells (TILs) and splenic cells (from same mouse) were isolated and stained with flow antibodies as indicated and ran in flow cytometer. (A) LILRB4 is expressed largely on macrophages within myeloid population. (B) Within CD4 T cells, expression of LILRB4 is higher on Treg (CD4+ Foxp3+) population compared to Teff (CD4+FoxP3−) population.

FIG. 4A-D shows LILRB4 is expressed largely on CD11b+ Tumor-associated macrophages (TAMs) and associated with markers known to express on suppressive TAMs. (A) t-SNE plot of MC38 infiltrating CD45+CD3− cells overlaid with color-coded clusters. (B) t-SNE plot of infiltrating CD45+CD3− cells overlaid with the expression of selected markers. (C) Frequency of clusters displayed on a per-mouse basis. Cluster numbers are indicated on x-axis. (D) Heatmap displaying normalized marker expression of each cluster.

FIG. 5A-D shows LILRB4 is expressed largely on Tregs and exhausted CD8 T cells. (A) t-SNE plot of MC38 infiltrating T cells overlaid with color-coded clusters. (B) t-SNE plot of infiltrating T cells overlaid with the expression of selected markers. (C) Frequency of clusters displayed on a per-mouse basis. Cluster numbers are indicated on x-axis. (D) Heatmap displaying normalized marker expression of each T cell cluster.

FIG. 6A-B shows B16/F10 Tumor injected mice survive longer when injected with polyclonal anti-LILRB4 antibody. (A) Mice were challenged with B16/F10 cells on right flanks and were given intratumoral treatments as shown. (B) Survival of mice in each treatment groups were monitored. Data are representative of 2 independent experiments with 7-10 mice per group. ***p<0.001 (Mantel-Cox test).

FIG. 7A-D shows anti-LILRB4 antibody treatment increases CD3T cells, CD8 T cells, CD4Teff frequency and decreases Treg frequencies in tumor microenvironment. Mice were challenged with B16/F10 cells and were given indicated treatments, cells from tumors were harvested and stained with indicated antibodies. Cumulative frequencies of CD3 T cells as percentages of CD45+ cells (A), CD8 T cells as percentages of CD3+ T cells (B), CD4 Teff cells as percentages of CD4+ T cells (C), and (D) CD4 Treg as percentages of CD4 T cells from 2 of 3 independent experiments. Error bars represent the mean±SD. *p<0.05, **p<0.01, (Student's t-test).

FIG. 8A-D shows anti-LILRB4 antibody treatment increases both CD8+ T cell and CD4+Eff to Treg ratio in tumor microenvironment. Mice were challenged with B16/F10 cells and were given indicated treatments, cells from tumors were harvested and stained with indicated antibodies. (A) CD8/Treg, (B) CD4 Teff/Treg, (C) CD8+Ki67+/Treg and (D) CD8+GzB+/Treg ratios in B16/F10 tumors in each group.

FIG. 9A-C shows expression of GP49B (LILRB4) in other murine tumor models. (A) Mice were challenged with B16/F10, mT5, RENCA, 4T1, MC38, MB49, TrampC2 cells. Cells from tumors were harvested and stained with indicated antibodies. (B) Spontaneous prostate cancer tumor model Tramp (Transgenic Adenocarcinoma of the mouse prostate) mice and naïve WT mice were sacrificed, their prostate tissues were isolated, digested, single cell suspension was made and stained with indicated antibodies. (C) Mice were challenged with TrampC2 tumor model subcutaneously on right flank, tumors were isolated, digested and stain with indicated antibodies.

FIG. 10A-C shows individual tumor growth and survival in LILRB4 knockout mice (B16-F10). WT and LILRB4KO mice were challenged with B16/F10 tumor. Tumor growth and survival of mice in each group was monitored. (A) Schematic diagram of tumor challenge. (B) Average tumor growth and (C) survival of mice in each group. Data are representative of 3 or 4 independent experiments with 5-10 mice per group. ***p<0.001 (Mantel-Cox test). (Student's t-test for tumor burden).

FIG. 11A-B shows decreased tumor growth and increased survival in LILRB4 knockout mice when challenged with mT5 (pancreatic tumor model). WT and LILRB4KO mice were challenged with mT5 tumor. Tumor growth and survival of mice in each group was monitored. (A) Individual tumor growth and (B) survival of mice in each group. Data are representative of 3 or 4 independent experiments with 5-10 mice per group. *p<0.05 (Mantel-Cox test for survival), (Student's t-test for tumor burden).

FIG. 17A-B shows expression of LILRB4 in tumor in cancer patients. Tumor digests from different tumor patients were stained with indicated antibodies, (A) LILRB4 expression on intratumoral CD45+ cells in three melanoma patients. (B) LILRB4 expression in intratumoral cells of renal cell carcinoma (RCC) and Triple negative breast cancer cells. FMO (Fluorescence minus one) control: This antibody mix does not have LILRB4 antibody but all other antibodies.

FIG. 18A-C shows LILRB4+ T cells expresses higher inhibitory receptors in both human cancer and murine tumor model (B16/F10). Tumor digests from different tumor patients were stained with indicated antibodies (A) Melanoma (B) Triple negative breast cancer. (C) Mice were challenged with B16/F10 tumors and when tumor grows to 1000 mm$^3$, mice were sacrificed and tumors were isolated. Tumor-infiltrating cells (TILs) and splenic cells (from same mice) were isolated and stained with flow antibodies as indicated and ran in flow cytometer.

FIG. 20A-B shows high correlation of lilrb4 with many inhibitory receptors (A) and (B) immune related genes (TCGA database).

FIG. 22A-B shows changes in myeloid clusters after treatment with anti-LILRB4 antibody. The clusters that decreased in frequency after treatment with anti-LILRB4 antibody expressed markers associated with suppressive macrophages. (A) t-SNE plot of an equal number of CD45+ CD3− MC38 tumor-infiltrating cells from each group and overlaid with color-coded clusters. (B) Bar plot of frequency of clusters and heatmap displaying normalized marker expression of each cluster. Cluster numbers are indicated on x-axis.

FIG. 23A-B shows changes in T cell clusters after treatment with anti-LILRB4 antibody. CD4+ Teff cell clusters increased in frequencies whereas exhausted CD8 T cell cluster decreased in frequency. (A) t-SNE plot of an equal number of MC38 tumor-infiltrating CD3+ T cells from each group and overlaid with color-coded clusters. (B) Bar plot of frequency of T cell clusters and heatmap displaying normalized marker expression of each cluster. Cluster numbers are indicated on x-axis.

DESCRIPTION OF ILLUSTRATIVE EMBODIMENTS

Figure 12:
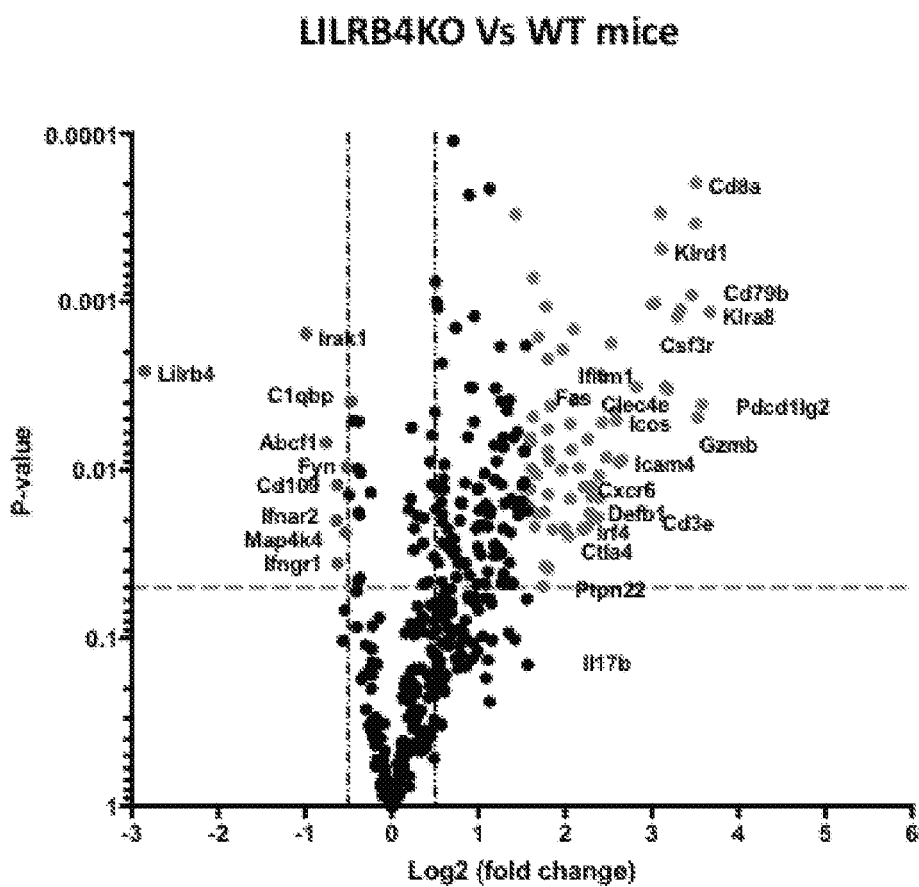
FIG. 12 shows expression of immune-related genes which are upregulated in LILRB4KO compared to WT mice. WT and LILRB4KO mice were challenged with B16/F10 tumor. Tumors were dissected when tumor grows to a 1000 mm$^3$, digested, tumor-infiltrating cells were isolated by ficoll density-gradient spin and RNA was extracted for nanostring assay and analysis.

In certain embodiments, the present disclosure provides anti-LILRB antibodies which may be used, for example, in the treatment of cancer. The anti-LILRB antibody may be a monoclonal antibody. The anti-LILRB antibody may be administered in combination with an additional therapy, such as chemotherapy and/or an immune checkpoint inhibitor, such as to treat cancer. In some aspects, the cancer is a melanoma. In further cases, the cancer is a leukemia such as AML. The present methods may target the LILRB pathway to inhibit cancer cell growth and/or stimulate and anti-cancer cell immune response in a subject.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

"Subject" and "patient" refer to either a human or non-human, such as primates, mammals, and vertebrates. In particular embodiments, the subject is a human.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

II. Lilrb4-Binding Antibodies

In certain embodiments, an antibody or a fragment thereof that binds to at least a portion of LILRB4 and inhibits LILRB4 activity are contemplated. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-LILRB4 antibody is a monoclonal antibody or a humanized antibody. In particular aspects, the anti-LILRB4 antibody is an antibody having the following sequences.

An antibody heavy chain comprising the CDRs. HCDR1 GFMFSSYW (SEQ ID NO: 1). HCDR2 INKDVTTT (SEQ ID NO: 2) and HCDR3 VRNHGSRYAYFDV (SEQ ID NO: 3). In some aspects, the antibody heavy chain comprises the VH sequence of SEQ ID NO: 10

EVKLVESGGGLVKPGGSLKLSCAASGFMFSSYWMNWVRQAPGKRLEWVGD

INKDVTTTNYSPSVKGRFTISRDNAKSILYLQMNSVKSEDTATYYCVRNH

GSRYAYFDVWGQGIQVTVSS

In further aspects, the VH sequence is encoded by a polynucleotide sequence of SEQ ID NO: 13:

GAAGTGAAGCTGGTGGAGTCTGGTGGTGGCCTGGTGAAACCTGGAGGGTC

CCTGAAACTCTCCTGTGCTGCCTCTGGATTCATGTTCAGTAGCTACTGGA

TGAACTGGGTCCGCCAGGCTCCTGGCAAGCGGCTGGAGTGGGTTGGAGAC

ATTAATAAAGATGTCACTACCACAAACTATTCACCATCCGTGAAGGGCCG

CTTCACCATCTCTAGAGACAATGCCAAGAGTATTCTGTACCTGCAAATGA

ACAGTGTGAAGTCTGAGGACACCGCCACTTATTACTGTGTTAGAAACCAC

GGTAGCCGCTATGCTTACTTTGATGTCTGGGGCCAGGGGATCCAGGTCAC

CGTCTCCTCA

An antibody light chain comprising the CDRs: LCDR1 TQHRTFY (SEQ ID NO: 4), LCDR2 VNSDGSQ (SEQ ID NO: 5) and LCDR3 GVNYESGKQYGYV (SEQ ID NO: 6). In some aspects, the antibody light chain comprises the VL sequence of SEQ ID NO: 11:

QPVLTQSPSASASPGASVRLTCTLSTQHRTFYIEWYQQYPDKAPKYVMKV

NSDGSQYKGDGIPDRFSGSSSGAHRYLTISNIQSEDEADYICGVNYESGK

QYGYVFGSGTQVTVL

In further aspects, the VL sequence is encoded by a polynucleotide sequence of SEQ ID NO: 14:

CAACCTGTGCTGACTCAGTCACCCTCTGCCTCTGCCTCCCCGGGAGCCTC

AGTCAGACTCACCTGCACCTTGAGTACTCAGCACAGAACCTTCTACATAG

AATGGTATCAGCAATATCCAGACAAGGCTCCTAAGTATGTGATGAAAGTT

AATAGTGATGGAAGTCAATACAAGGGGGATGGGATCCCTGATCGCTTCTC

TGGCTCCAGTTCTGGGGCTCATCGCTACTTAACAATCTCCAACATTCAGT

CTGAAGATGAAGCTGACTACATCTGTGGTGTTAATTATGAAAGTGGTAAA

CAATATGGGTATGTTTTTGGCAGCGGAACCCAGGTCACCGTCCTAG

An antibody light chain comprising the CDRs: LCDR1 NGISVGGKN (SEQ ID NO: 7); LCDR2 YYSDSDK (SEQ ID NO: 8) and LCDR3 SIYESNTWV (SEQ ID NO: 9). In some aspects, the antibody light chain comprises the VL sequence of SEQ ID NO: 12:

QSILTQPPSISESLGSTARLTCTLNNGISVGGKNIYWYQQMAGSVPRLFL

YYYSDSDKELGPGVPNRDSGSKDTSKKAANLQISELQVEDEAVCFCSIYE

SNTWVFGSGTKVTVL

In further aspects, the VL sequence is encoded by a polynucleotide sequence of SEQ ID NO: 15:

CAGTCTATATTGACACAACCACCCTCCATCTCTGAGTCTCTTGGATCAAC

AGCCAGACTCACCTGCACCCTGAATAATGGCATCAGTGTTGGTGGTAAAA

ATATTTACTGGTACCAGCAAATGGCGGGGAGTGTTCCTCGTTTGTTCCTG

TACTACTACTCAGATTCAGACAAGGAGCTGGGGCCTGGAGTCCCCAACAG

AGACTCTGGATCCAAAGATACCTCCAAAAAAGCTGCAAATTTGCAGATCT

CTGAGCTACAGGTGGAGGATGAGGCTGTGTGTTTCTGTTCCATCTATGAA

AGTAATACTTGGGTGTTCGGTTCAGGCACCAAAGTGACTGTCCTAG

Thus, an antibody of the embodiments can comprise VH polypeptide provided above paired with either of the provide VL polypeptides. In some aspects, an antibody comprises one pair of VH and the first VL polypeptide and a second pair of VH and the second VL polypeptide.

Thus, by known means and as described herein, polyclonal or monoclonal antibodies, antibody fragments, and binding domains and CDRs (including engineered forms of any of the foregoing) may be created that are specific to LILRB4, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made.

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a LILRB4 polypeptide or a portion thereof, in order to produce antibodies specific for LILRB4. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a LILRB4 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells ($CD45^+CD5^-CD19^+$) may be isolated from freshly prepared rabbit peripheral blood mononuclear cells of immunized rabbits and further selected for LILRB4 binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. LILRB4 specific binding Fab may be selected out through multiple rounds enrichment panning and sequenced. Selected LILRB4 binding hits may be expressed as full-length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837, 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946, 546, which is incorporated herein by reference.

It is fully expected that antibodies to LILRB4 will have the ability to neutralize or counteract the effects of LILRB4 regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds LILRB4.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against LILRB4, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

III. Methods of Treatment

Certain aspects of the present embodiments can be used to prevent or treat a disease or disorder associated with LILRB4 signaling. Signaling of LILRB4 may be reduced by any suitable drugs to prevent cancer cell proliferation. Preferably, such substances would be an anti-LILRB4 antibody.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma. In particular embodiments, the cancer is breast cancer.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

A. Pharmaceutical Compositions

Also provided herein are pharmaceutical compositions and formulations comprising a LILRB4-binding antibody and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). In one aspect, a sHASEGP is combined with one or more additional glycosaminoglycanases such as chondroitinases.

B. Combination Therapies

In certain embodiments, the compositions and methods of the present embodiments involve a LILRB4-binding antibody in combination with at least one additional therapy.

The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

A LILRB4-binding antibody may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below a LILRB4-binding antibody is "A" and an anti-cancer therapy is "B":

ylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin: spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; eto-

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine;

vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation, and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs and may be used in combination therapies. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. Exemplary ADC drugs include ADCETRIS® (brentuximab vedotin) and KADCYLA® (trastuzumab emtansine or T-DM1).

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, erb b2 and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis, Plasmodium falciparum*, dinitrochlorobenzene, and aromatic compounds); cytokine therapy, e.g., interferons α, β, and γ, IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies. Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody that may be used. Pembrolizumab, also known as MK-3475, Merck 3475, lambrolizumab, KEYTRUDA®, and SCH-900475, is an exemplary anti-PD-1 antibody. CT-011, also known as hBAT or hBAT-1, is also an anti-PD-1 antibody. AMP-224, also known as B7-DCIg, is a PDL2-Fc fusion soluble receptor.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or $V_H$ and/or $V_L$ domains derived therefrom) suitable for use in the present methods can be generated using methods well known in the art. Alternatively, art recognized anti-CTLA-4 antibodies can be used. An exemplary anti-CTLA-4 antibody is ipilimumab (also known as 10DI, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin.

IV. Articles of Manufacture or Kits

An article of manufacture or a kit is provided comprising a LILRB4-binding antibody is also provided herein. The article of manufacture or kit can further comprise a package insert comprising instructions for using the antibody to treat or delay progression of cancer in an individual or to enhance immune function of an individual having cancer. Any of the antibodies or combination therapies described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—LILRB4 Antibody Characterization

A vast range of co-receptors/co-inhibitors are expressed on tumor-infiltrating cells and have not been studied in tumor context, which has led to a search for new targets. To identify such targets, transcriptomics and proteomics approaches were employed. RNA expression of number of inhibitory receptors were analyzed in tumor microenvironment (TME) in metastatic melanoma model B16-F10 by nanostring (FIG. 1A). The inventors' approach identified Lilrb4, an ITIM containing receptor to be expressed highly in tumor microenvironment. Lilrb4 gene expression was even higher than pdcd-1 gene expression in B16 melanoma mouse model, which suggested that this receptor might be playing an important role in tumor microenvironment. The gene expression of this receptor was also analyzed in tumors from melanoma patients by nanostring analysis. The nanostring gene expression data showed a relatively high expression of lilrb4 in human melanoma (FIG. 1B). Multicolor flow cytometry was then employed to analyze expression of a panel of inhibitory receptors on tumor infiltrating T cells in late stage in a B16F10 melanoma mouse model. High expression of LILRB4 was observed on tumor-infiltrating T cells and this expression was comparable to another known inhibitory receptor PD-1 (FIG. 2A). The expression of LILRB4 increases on CD4 T cells with the increase in tumor size as it was found an increased expression of LILRB4 on CD4 T cells at day 22 compared to day 14 after B16-F10 challenge (FIG. 2B). This further confirmed the hypothesis that LILRB4 might have an important role to play in tumor microenvironment, thus LILRB4 (GP49B) inhibitory receptor was identified as a potential target for immunotherapy with its high expression on tumor-infiltrating cells which was comparable to PD-1 and CTLA-4 (FIGS. 1 & 2). Expression of this receptor was also analyzed on various tumor-infiltrating cells by flow cytometry and the analysis showed that LILRB4 was highly expressed on CD11b+F-4/80+ macrophage cell within myeloid population (FIG. 3A). Within CD4+ t cells, the expression of this receptor was comparatively more on CD4+FoxP3+ Treg population compared to CD4+FoxP3− T effector population (FIG. 3B). To further look at the LILRB4 expression in tumor-infiltrating cells deeply at various cell subsets level, mass cytometry (Cytof) was used, in which more than 30 markers could be studied simultaneously. Myeloid and lymphoid panels were developed. Tumor-infiltrating cells obtained from digested MC38 tumors were stained with metal-labeled antibodies in each panel, barcoded and ran on cytof machine (Helios). The data obtained was analyzed using Cyt2 software on Matlab platform. Myeloid panel identified total number of 15 clusters with frequency greater than 0.5% which includes multiple populations of monocyte/macrophages (clusters 1-6 and 9-12), DC clusters (7, 8 and 13), eosinophil cluster (cluster 14) and neutrophil cluster (cluster 15)(FIG. 4). LILRB4 was expressed on most clusters, other than cluster 13 and and 14. Monocyte/macrophage clusters had the highest expression levels of LILRB4 although it was variable amongst different clusters. Three clusters had highest expression of LILRB4 amongst LILRB4-expressing clusters. These clusters were cluster 6 (CD11b$^+$F4/80$^{low}$Arg-1$^{high}$ CCR2$^{high}$CX$_3$CR1$^+$Ly6C$^{high}$cluster), cluster10 (CD11b$^+$F4/80$^{high}$Arg1$^+$IDO$^{high}$CD204$^{high}$CD64$^+$ CX$_3$CR1$^{high}$CD206$^+$ CCR2$^+$ Ly6C+ cluster) and cluster11 (CD11b$^+$ F4/80$^{low}$ CD68$^{high}$ CX$_3$CR1$^{low}$ CD163$^+$ Arg-1$^+$ IDO$^+$CD204$^+$CD64$^+$PDL1$^{high}$PD1L2$^{high}$) suggesting expression of this receptor on macrophages with suppressive phenotype. To comprehensively characterize T cell population, a staining panel was designed with T cell subset markers (CD4, CD8 and FoxP3), NK1.1, TCR gamma-delta and various inhibitory receptor markers. A high-resolution map of phenotypically defined tumor-infiltrating T cells population was developed using unsupervised clustering and eleven clusters were identified with relative frequency greater than 0.5% which includes three CD4 Treg clusters, two CD4 Teff clusters and three CD8 T cell clusters (FIG. 5). Amongst T cells, LILRB4 expression was highest on Tregs. There were three clusters of Tregs, KLRGR1$^{high}$ICOS$^{high}$TGFβ$^{high}$, KLRG1$^{high}$ICOS$^+$TGFβ$^{low}$ and KLRG1$^{low}$ICOS$^{high}$TGFβ$^{high}$. The highest expression of LILRB4 was on KLRG1$^{high}$ICOS$^{high}$TGFβ$^{high}$ Treg cluster and lowest expression was on KLRG1$^{low}$ICOS$^{high}$TGF$^{high}$ cluster. There were two clusters of CD4 effector T cells, PD-1$^{high}$LAG3$^+$ and PD-1$^−$LAG3$^−$. Amongst these two clusters of CD4 effector T cells, the expression of LILRB4 was higher on PD-1$^{high}$LAG3$^{high}$ CD4 Teff cells. There were three distinct CD8 T cells clusters, amongst these 3 clusters, LILRB4 is expressed only on PD-1$^{high}$LAG3$^{high}$Tim-3$^{high}$ clusters. These results suggest that LILRB4 expression is associated with other immune inhibitory receptors. They also confirm the earlier observation that LILRB4 is expressed on regulatory T cells and CD8 T cells with exhausted phenotype.

Figure 13:
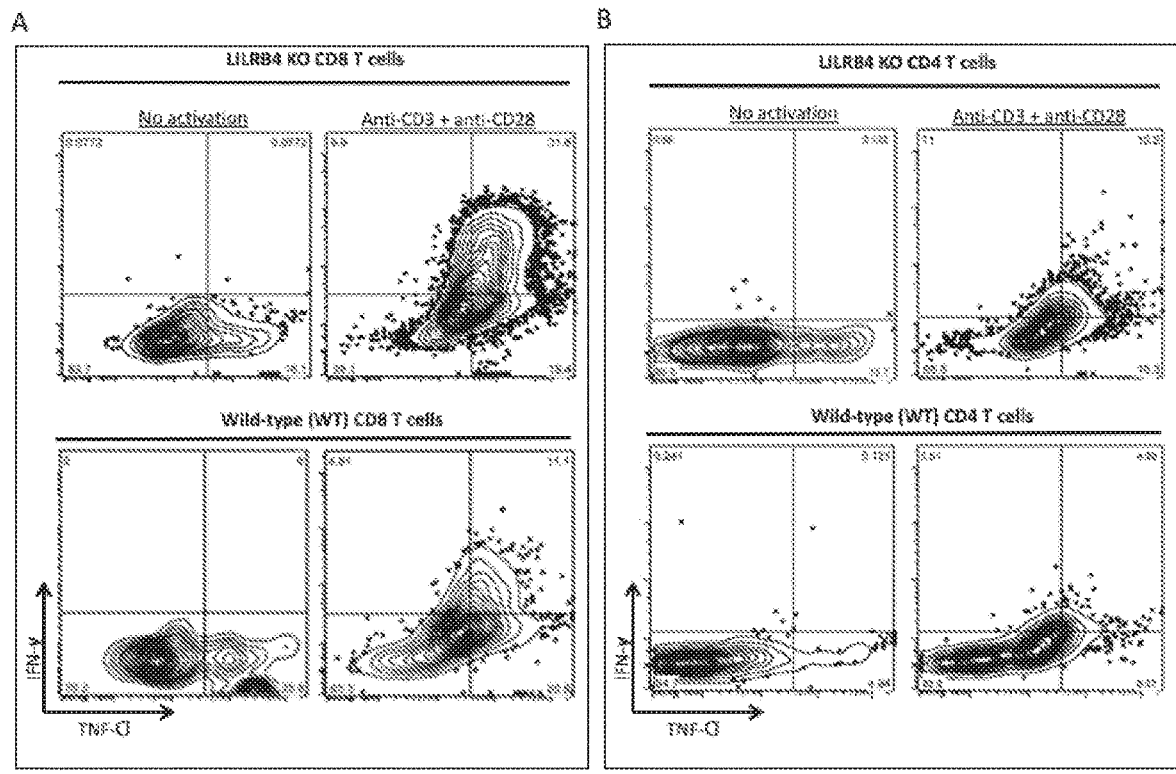
FIG. 13A-B shows increased IFN-γ and TNF-α secretion from LILRB4 knock-out CD8 and CD4 T cells on activation with anti-CD3 and anti-CD28 antibodies. Naïve spleens were isolated from LILRB4KO and WT mice. Single cell suspensions were prepared from spleens, red blood cells were lysed with RBC lysis buffer, and splenocytes were filtered through cell strainers. Naïve untouched total T cells were isolated, stimulated in-vitro with anti-CD3 (1.25 µg/ml) and anti-CD28 (1.25 µg/ml) antibodies for 72 hours. Cells were then stained with indicated antibodies. (A) CD8 T cells and (B) CD4 T cells.
Figure 14:
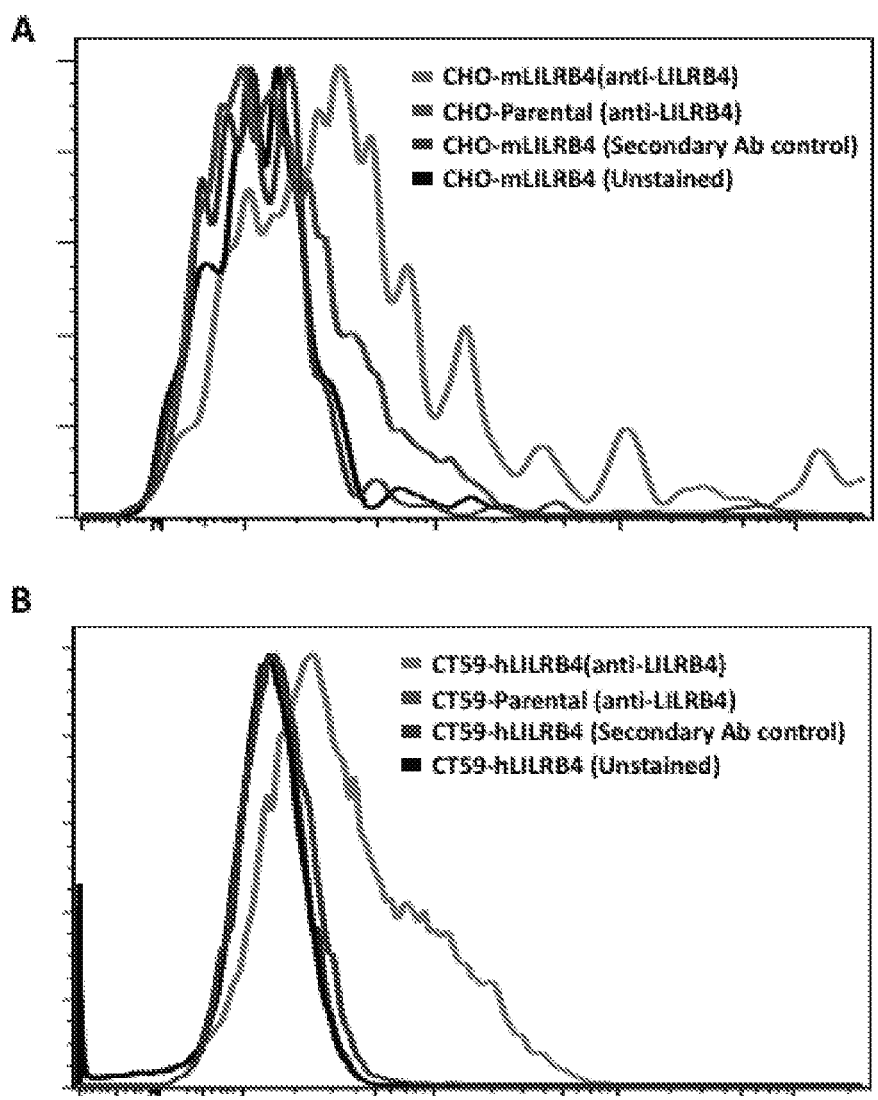
FIG. 14A-B shows binding of anti-LILRB4 monoclonal antibody with murine and human LILRB4 over-expressed cell lines. Cells were isolated from tissue culture plates, stained with hamster anti-LILRB4 antibody and then with secondary anti-hamster antibody and ran on flow cytometer. (A) CHO cells transfected with mouse LILRB4 (CHO-mLILRB4) and CHO-parental cells. (B) CT59 cells transfected with human LILRB4(CT59-hLILRB4) and CT59-parental.
Figure 15:
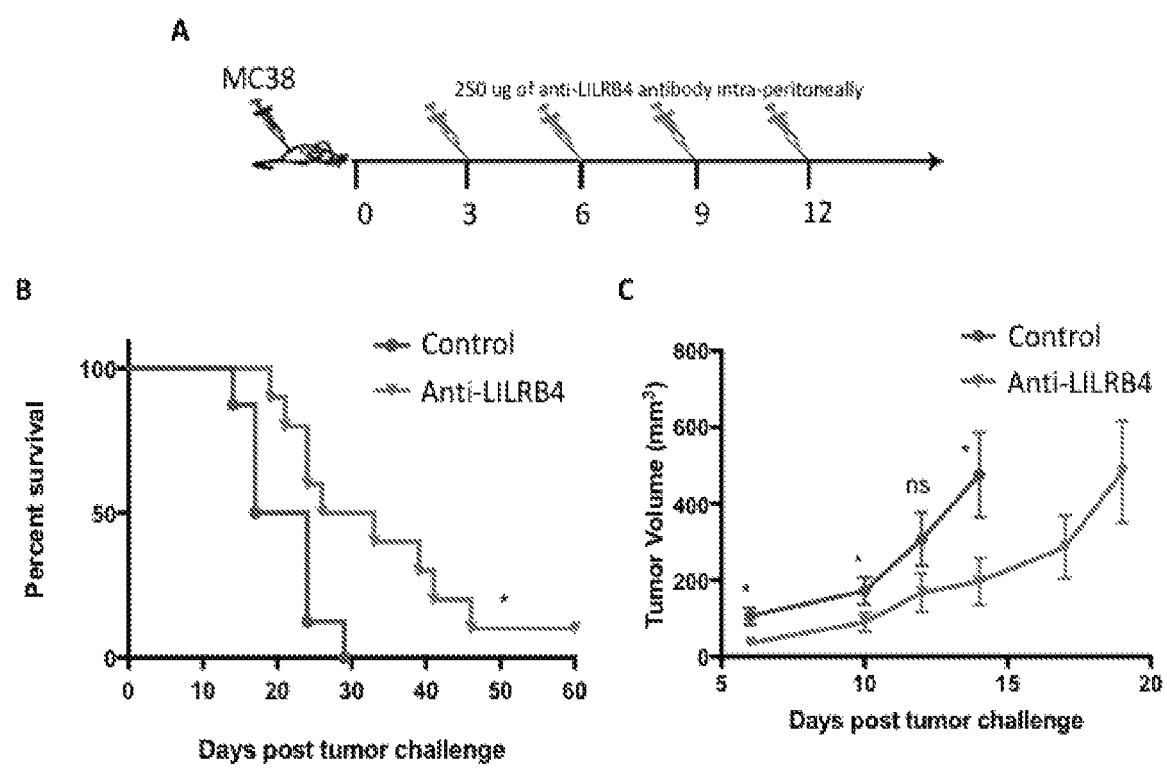
FIG. 15A-C shows increased survival and decreased tumor burden in mice challenged with MC38 and treated with LILRB4 monoclonal antibody. Mice were challenged with MC38 tumor model subcutaneously on right flank. Mice were given intraperitoneal treatment of antibody as shown. (A) Schematic diagram of tumor challenge. (B) Survival and (C) tumor burden in each treatment groups were monitored. Data are cumulative of 2-3 independent experiments with 5-10 mice per group. *p<0.05 (Mantel-Cox test for survival), (Student's t-test for tumor burden).
Figure 16:
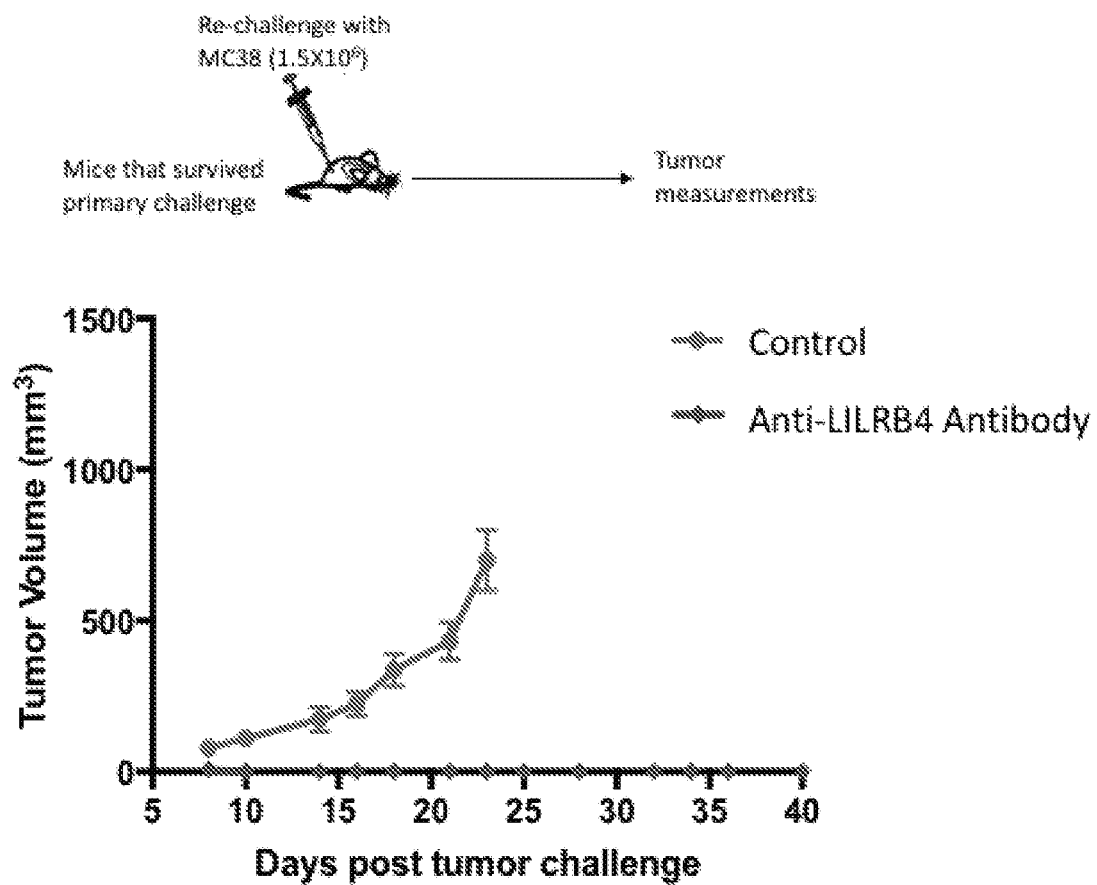
FIG. 16 shows anti-LILRB4 antibody induces immunological memory. Mice that survived primary MC38 challenge and had been earlier treated with anti-LILRB4 antibody were re-challenged with 5 times more MC38 cells and left untreated. The blue line represents the average tumor burden of memory mice whereas red line represents naïve mice with no earlier tumor challenge or treatment, which served as a control.
Figure 19A:
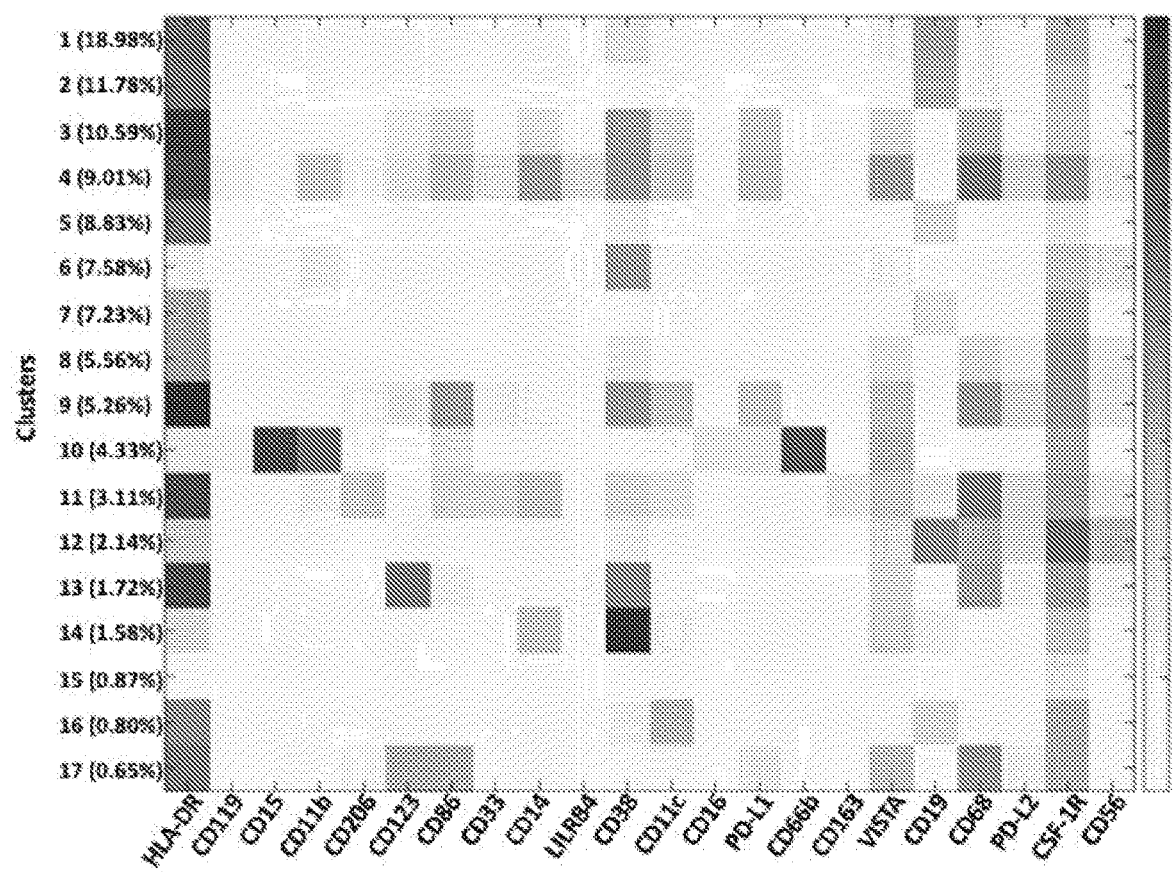
FIG. 19A-B both panels show Heatmap displaying normalized LILRB4 expression in each myeloid cell clusters obtained by mass cytometry (CyTOF).
Figure 19B:
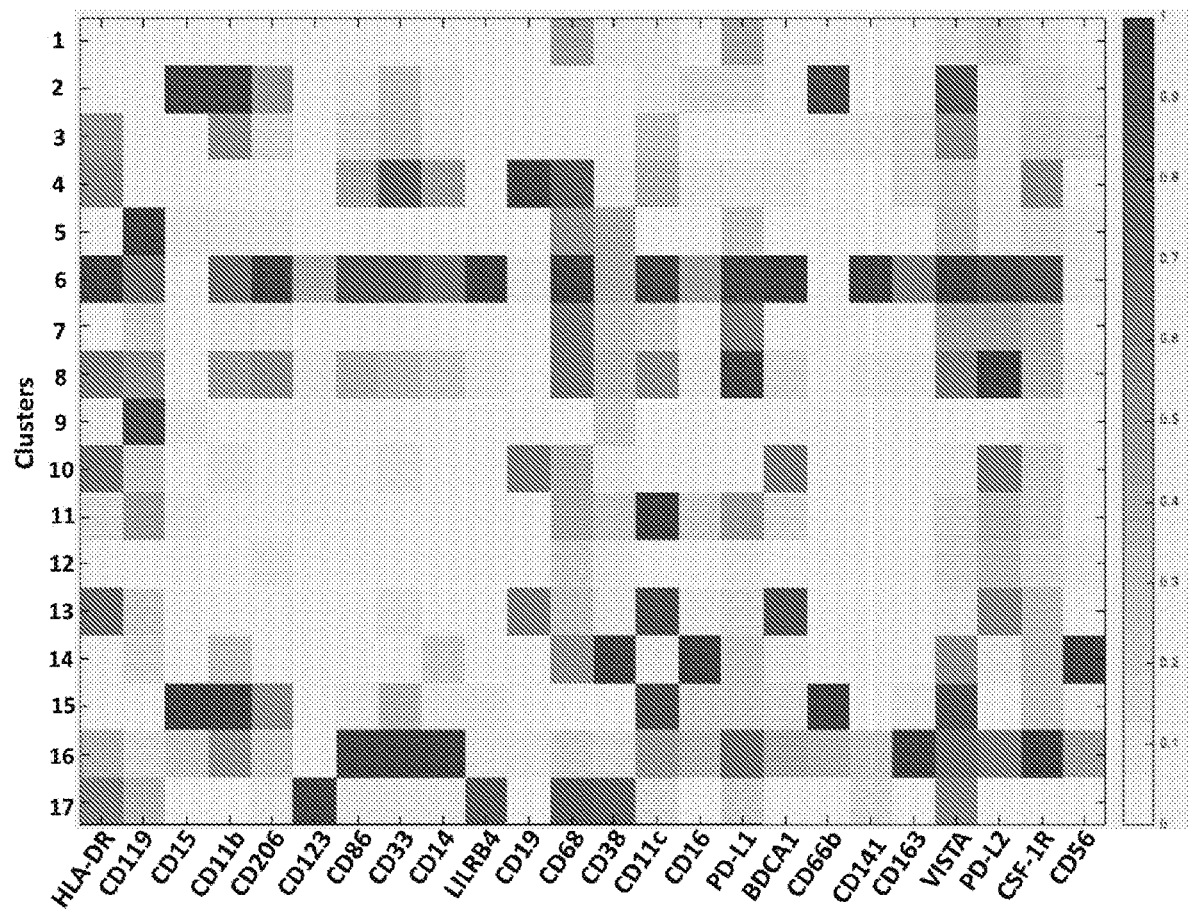
Figure 21:
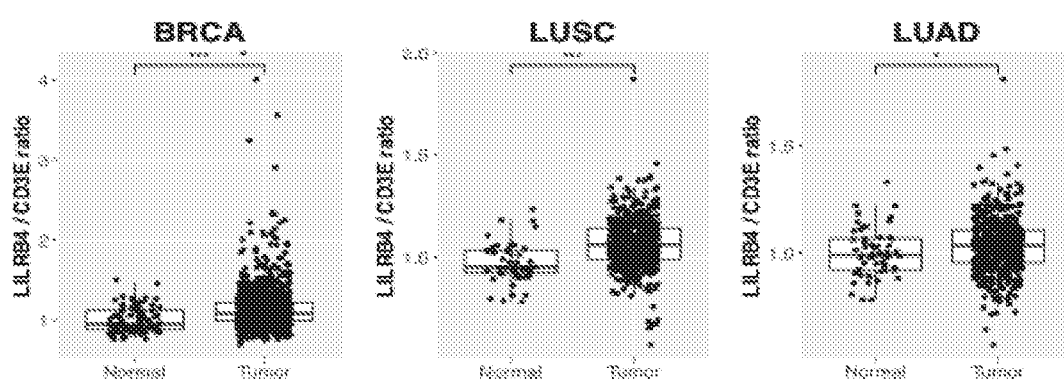
FIG. 21 shows lilrb4 has enhanced expression in human cancers compared to healthy individual (TCGA database). BRCA: Breast Cancer; LUSC: Lung Squamous Cell Carcinoma; LUAD: Lung Adenocarcinoma

To understand the role of this receptor in tumor microenvironment, tumor burden and survival were analyzed after challenging mice with B16/F10 and further treating them with intratumoral injections of goat polyclonal antibodies against LILRB4 and isotype control (FIG. 6A). Tumor growths were significantly reduced in mice injected with antibodies against this receptor compared to tumor growths in mice injected with isotype control (goat IgG) and vehicle control (FIG. 6B). The functional effect of antibody treatment was assessed on tumor-infiltrating T cells. Mice were challenged with B16/F10 tumors and treated with anti-LILRB4 antibody and isotype control. Two days after the last treatment at day 14, tumors were isolated, digested and single cell suspensions were made. These cells were then stained with flow cytometry antibodies as indicated. To understand the effect of anti-LILRB4 antibody on TILs, the frequencies of each subset of T cells within tumors was analyzed. There was a significant increase in percentages and population of CD3+ T cell population within tumors in anti-LILRB4 antibody treated group compared to isotype control treated group (FIG. 7A). CD8 T cell and CD4+ FoxP3− Teff percentages also went up within tumors in anti-LILRB4 treatment group compared to the Isotype control group (FIGS. 7B and C). However, Interestingly, there was a decrease in frequency of CD4+FoxP3+ Treg in anti-LILRB4 treatment group (FIG. 7D). CD8 T cells and CD4 Teff to Treg ratios are predictive of therapeutic efficacy of treatment in the B16 melanoma model. Therefore, it was important to look at those ratios and it was found that a significant increase in both CD8 T cells and CD4 effector T cells to Treg ratios within tumour in anti-LILRB4 antibody treated group (FIGS. 8A&B). CD8+Ki67+ and CD8+GzB+ to Treg ratio was also high in anti-LILRB4 antibody treated group suggested an increase in proliferation as well as cytotoxicity of CD8 T cells after anti-LILRB4 antibody treatment (FIGS. 8C&D). To further confirm that LILRB4 expression is not tumor-specific, its expression was analysed in various known murine tumor models such as mT5 (Pancreatic tumor), RENCA (Renal Carcinoma), 4T1 (Breast Cancer), MC38 (Colon Cancer), MB49 (Bladder Cancer), TrampC2 (Prostate Cancer). Its expression was also analysed in tumor-infiltrating cells of prostate of spontaneous prostate tumor mice model, TRAMP and compared it with cells from prostate of naïve mice. It was found that LILRB4 is expressed widely in tumor-infiltrating CD45+ cells of all these tumor models (FIGS. 9A &B). The expression of LILRB4 was further analyzed in both CD4T cells and CD8T cells in another tumor model Tramp-C2. It was found that similar patterns of expression of LILRB4 in Tramp-C2 model where the expression of LILRB4 was higher on tumor-infiltrating CD4 T and CD8 T cells compared to splenic CD4 and CD8 T cells (FIG. 9C). To confirm role of LILRB4 in antitumor immunity, LILRB4 knock-out (LILRB4 KO) mice were challenged with B16/F10 or mT5 tumor model. Tumor burden and survival was measured and compared with wild-type (WT) control. This result suggests a decrease in tumor burden and increase in survival in LILRB4 knock out mice compared to wild-type (WT) control (FIGS. 10 & 11). mRNA extracted from tumor-infiltrating cells was analyzed from LILRB4 ko and wild-type (WT) mice which were challenged with B16/F10 cells. A number of immune-related cells were differentially upregulated in LILRB4KO mice which are associated with anti-tumor pathways such as CD8a and Gzmb (FIG. 12). Splenic T cells isolated from LILRB4 ko mice and wild-type (WT) mice were also activated in-vitro and found an increased secretion of IFN-γ and TNF-α from LILRB4 ko CD8 and CD4 T cells compared to WT T cells further confirming inhibitory role played by LILRB4 (FIG. 13). Encouraged by the results with goat polyclonal antibodies and LILRB4 knock-out murine models, monoclonal antibodies against mouse LILRB4 were developed and the antibody clone was identified which exhibit binding to LILRB4 overexpressed cells by flow cytometry. This antibody showed binding to both murine LILRB4 and human LILRB4 over-expressed cells suggesting cross-reactivity of this antibody (FIGS. 14A &B). After selection of hybridoma candidate master cells, antibody was purified from this clone and injected in mice after they were challenged with MC38 murine tumor model (FIG. 15A). The mice which were injected with anti-LILRB4 antibody showed significant reduction in tumor burden and increased survival (FIGS. 15B & C). The mice that survived primary MC38 tumor challenge after anti-LILRB4 antibody injection were re-challenged with five times dose of MC38, and left untreated. Mice that were earlier treated with anti-LILRB4 antibody completely rejected higher dose of tumor rechallenge (FIG. 16). LILRB4 cell surface protein expression was analyzed in tumor samples of melanoma, renal cell carcinoma and breast cancer patients by multi-color flow cytometry. It was found to be highly expressed on tumor-infiltrating CD45+ cells (FIG. 17). LILRB4 is expressed on both lymphoid and myeloid compartments in melanoma and breast cancer patients and LILRB4+CD3+T cells show more exhausted or dysfunctional T cell profile shown by higher expression of CTLA-4, PD-1 and LAG-3 on these cells compared to LILRB4-CD3+T cells (FIGS. 18 A&B). Similarly, LILRB4+CD4+ T cells from tumors of B16/F10 challenged mice showed increased expression of many inhibitory receptors compared to LILRB4-CD4+ T cells suggesting association of expression of this receptor with exhausted phenotype (FIG. 18C). Cell surface protein expression data of LILRB4 in melanoma patients by mass cytometry (CyTOF) analysis suggest that within myeloid population, LILRB4 is highly expressed on clusters 6, 8 and 17, low-levels on cluster 15 and 16 (FIG. 19). Cluster 6 is CD11b+ CD68$^{high}$CD206$^{high}$PD1-L1$^{high}$PD1-L2$^{high}$VISTA$^{high}$CSF-1R$^{high}$ cluster, Cluster 8 is CD11b+CD68+CD206+PD1-L1$^{high}$PD1-L2$^{high}$VISTA+CSF-1R+ cluster, Cluster 17 is CD11b-CD68+CD123$^{high}$CD38+VISTA+CD11c+ DC subset. This expression pattern suggests that LILRB4 in human tumor is also expressed highly on suppressive tumor-associated macrophages (TAM). To understand the extent of expression of LILRB4 in different tumors and its correlation with various other immune-related molecules, a bioinformatics approach was used to analyze expression data from the Cancer Genome Atlas database (TCGA) in different cancer types, like Bladder Cancer (BLCA), Breast cancer (BRCA), Lung squamous cell carcinoma (LUSC), Lung adenocarcinoma (LUAD) and Skin cutaneous melanoma (SKCM). LILRB4 was highly correlated with other inhibitory molecules specially PD-1 (Spearman's rank correlation coefficient (ρ=0.67-0.84) and TIM-3 (HAVCR2) (Spearman's rank correlation coefficient (ρ=0.84-0.95) in different tumor types (FIG. 20A). LILRB4 was also highly correlated with cytotoxic granules like granzymes (GZMA, GZMB and GZMK) and perforin (PRF1), interferon-γ (IFNG) and with interleukins IL-12 (IL-12RB1) and IL-2 (IL2RB and IL2RG) suggesting its important functional role in T cell immunity (FIG. 20 B). There was also a significant increase in LILRB4: CD3ε expression ratio in BRCA, LUSC and LUAD tumor samples compared to normal tissue samples indicating the up regulation of LILRB4 in broad range of tumors compared to normal tissue (FIG. 21).

The effects of anti-LILRB4 monoclonal antibody treatment on tumor-associated myeloid cells was also analyzed. To this end, mice were treated with anti-LILRB4 antibody on different days, tumors were dissected, cells were isolated from tumors and stained with cytof antibodies and ran on cytof machine (Helios). Twenty clusters were identified using myeloid panel amongst CD45+CD3− tumor-associated cells. These clusters were annotated as fourteen clusters of monocytes/macrophages (Clusters 1-8, 12, 14-16), four DC clusters (9, 11, 13 and 17), one neutrophil cluster (cluster 20) and one eosinophil cluster (cluster 10) (FIG. 22). Amongst monocytes/macrophage clusters, clusters 1, 5, 6 and 12 decreased in frequency after the treatment with anti-LILRB4 monoclonal antibody. Cluster 1 is CD11b+F4/80+CCR2$^{high}$CX$_3$CR1$^{high}$ Arg1+IDO$^{high}$CD204$^{high}$VISTA+ LILRB4$^{high}$PDL1+ cluster, cluster 5 is CD11b+F4/80$^{low}$ CCR2$^{high}$Arg1+CX$_3$CR1+IDO+CD204+LILRB4+Ly6C$^{high}$ cluster, cluster 6 is CD11b+F4/80$^{low}$ CCR2$^{high}$Arg1$^{high}$CX$_3$CR1+IDO+CD204+ LILRB4$^{high}$ Ly6C$^{high}$ cluster, cluster12 is CD11b+F4/80$^{1+}$ CCR2+Arg1+ CX$_3$CR1+IDO+CD204+ LILRB4$^{high}$ cluster. The expression of Arginase1 (Arg-1), CX$_3$CR1 and IDO in these clusters suggest that these clusters are suppressive macrophage clusters. Also, the clusters which were decreased in frequency after anti-LILRB4 antibody had high surface expression of CCR2 and CX$_3$CR1+, which are associated with poor prognosis in tumors. Clusters 5 and 6 are identified as Ly6C$^{high}$ CCR2+ circulating monocytes clusters which are recruited to the tumor and become immunosuppressive TAM. The monocytes/macrophage clusters which were increased after the anti-LILRB4 monoclonal antibody include clusters 7, 8, 10, 14. Cluster 7 is LILRB4$^{low}$CD11b+F4/80−CD68+ CX$_3$CR1−MHCII+ICAM1+IDO−Arg1−CD11c+ cluster, Cluster8 is LILRB4$^{low}$CD11b$^{high}$F4/80+CD68+iNOS2+ Arg1−IDO$^{low}$PD1-L1$^{high}$CD14$^{high}$CD64+CD11c+, cluster 10 is CD11b+F4/80$^{low}$Siglec-F$^{high}$ eosinophils. Cluster 14 is LILRB4$^{low}$ MHCII+VISTA+CD14+CD40+ does not expresses either CD11b or CD11c and could be a B cell cluster. These clusters do not express phenotype associated with suppressive macrophages and therefore interestingly, reduction in the levels of suppressive phenotype clusters as described earlier and increase in non-suppressive macrophage clusters as described above suggest the change in tumor microenvironment from pro-tumor to anti-tumor after treatment with anti-LILRB4 monoclonal antibody.

Twelve clusters were identified using T cell panels amongst tumor-infiltrating CD3+ T cells. They were annotated as two clusters of Tregs (cluster 1 and 8), three clusters of CD4Teff cells (clusters 3, 7 and 11), four clusters of CD8 T cells (clusters 2, 6, 9 and 10), two clusters of NKT cells (clusters 4 and 5) and one γδ T cell cluster (cluster 12). Amongst Treg clusters, LILRB4$^{high}$ICOS$^{high}$KLRG1$^{high}$LAP-TGFβ$^{high}$ cluster decreased slightly in frequency whereas LILRB4$^{low}$ICOS$^{+}$KLRG1$^{+}$LAP-TGFβ$^{low}$ cluster showed slight increase after anti-LILRB4 antibody treatment. Amongst CD4$^{+}$Foxp3$^{-}$ T cell clusters, all clusters increased in frequency after anti-LILRB4 treatment. Amongst CD8 clusters, cluster 2 is Tim3$^{+}$LAG3$^{+}$PD1$^{+}$ exhausted CD8+ T cell cluster and this cluster has very significant decrease after anti-LILRB4 treatment. Clusters 6 and 9 also showed slight decrease and only cluster 10 was increased in ant-LILRB4 treatment group. Cluster 6 is PD-1$^{-}$CD127+Eomes+ whereas cluster 9 is Tim3$^{+}$LAG3$^{+}$PD1$^{+}$ exhausted CD8+ T cell cluster. Only one CD8 cluster, cluster 10 was increased and this cluster is naïve CD127+CD8+cluster. These results suggest that treatment with anti-LILRB4 antibody modulates CD4T cells towards more effector phenotype whereas there is a decrease in exhausted CD8 Tcells and increase in naïve CD8 T cells. As such, blockade of this receptor may be a useful approach for immunotherapy of cancer.

The results discussed herein illustrate that LILRB4 may be a good target for immunotherapy in human cancer and may be used as a therapy intervention against cancer, either on its own or in combination with checkpoint blockade antibodies.

Example 2—Materials and Methods

Mice 6-8-week-old C57BL/6 wild type mice were purchased from Jackson laboratory. All mice were housed under specific pathogen-free conditions in accordance with institutional guidelines. MD Anderson Cancer Center's Institutional Animal Care and Use Committee approved all animal experiments.

Cell Lines and Reagents

The mouse melanoma cell line B16/F10 were maintained as described previously (see, Van Elsas et al. 1999). The pancreatic cancer cell line mT5 was maintained as described previously (see, Boj et al., 2015. MC38 murine colon carcinoma cells were obtained from N. Restifo (National Cancer Institute) and cultured in DMEM supplemented with 10% FBS with Penicillin/Streptomycin(P/S). The chemically induced murine bladder carcinoma MB49 cell line was cultured in DMEM with 10% FBS and P/S. Murine renal adenocarcinoma cell line RENCA cell line were obtained from MDACC cell line core and maintained in DMEM with 10% FBS and P/S. The TRAMP-C2 cell line was derived from prostate tumor of a male TRAMP mouse and provided by Dr. N. Greenberg and maintained as described previously (see, Foster et al., 1997). The following antibodies were used for flow cytometry analysis of tumors. Anti-mouse CD4 (clone GK1.5), anti-mouse CD8 (clone 53-6.7), anti-mouse CD45.2 (clone104), anti-mouse F4/80 (clone BM8), anti-mouse I-A/I-E (clone M5/114.15.2), anti-mouse TNFα, anti-mouse CD11c (N418), anti-mouse CD19 (6D5), anti-mouse NK1.1 (PK136), anti-mouse Tim-3, anti-mouse CD160 (Clone 7H1) were purchased from Biolegend. Anti-mouse CD3 (clone 145-2C11), anti-mouse/human granzyme B (clone GB11), anti-human CD3, anti-Human CD45, anti-Human CTLA4, anti-human PD-1 were purchased from BD Biosciences. Anti-mouse Foxp3 (clone FJK-16s), anti-mouse PD-1 (clone J43), anti-mouse CD272 (BTLA), anti-mouse 2B4 (244.2), anti-mouse PD-1H (VISTA), Anti-mouse LAG-3, anti-mouse LILRB4, anti-mouse CD11b (clone M1/70), anti-mouse GR-1(clone 1A8), anti-Human CD279 (PD-1), anti-Human CD223 (LAG-3), anti-Human LILRB4 (ILT3) were purchased from eBioscience. Functional anti-mouse CD3e monoclonal antibody (Clone 500A2) and anti-mouse CD28 monoclonal antibody (37.51) were also purchased from eBiosciences. Goat polyclonal Anti-mouse LILRB4(GP49B) antibodies was purchased from Santa Cruz Biotechnology. Monoclonal anti-LILRB4 antibody hybridomas were generated in Armenian Hamster. Hybridomas were selected and supernatants from the resulting clones were screened by ELISA and their binding with the LILRB4-overexpressed cell lines by FACS. The selected clones were sent to BioXcell for large scale purification of antibodies.

Tumor Challenge and Treatment

Mice were given intradermal injections of 3×10$^5$ B16/F10 cells or subcutaneous injections of 1×10$^5$ mT5 cells, 3×10$^5$ MC38 cells, 2×10$^5$ MB49 cells, 2×10$^5$ RENCA cells and 4×10$^5$ 4T1 cells on their right flanks on day 0. Mice were then treated with intraperitoneal injections of monoclonal anti-LILRB4 antibody (250 μg) or intratumoral injections of polyclonal anti-LILRB4 antibody (50 μg) on days 3, 6, 9, and 12. For re-challenged memory experiments, mice that survived primary tumor challenge and had been earlier treated with anti-LILRB4 antibody therapy were re-challenged with 5 times dose of tumor cells and left untreated. In experiments in which mice would be sacrificed on day 14 to understand the mechanism, the initial injection of B16/F10 cells was doubled to 6×10$^5$ cells. These mice were sacrificed on day 14 to obtain tumors and draining lymph nodes or to analyze tumor growth. For the tumor burden or survival experiments, the mice were considered moribund when the tumor grew to 1000 mm$^3$ and humanely killed.

Tumor Processing and Flow Cytometry

For phenotypic and functional analysis of tumor infiltrating cells, mice were challenged and treated as described above. Mice from each treatment group were humanely killed on day 14, and their tumors and spleen were isolated. Isolated tumors were weighed, mechanically dissected, and then digested with Dnase I and Liberase TL (Roche) at 37° C. for 30 minutes and then filtered through 70 μm nylon cell strainer. Spleen were mechanically dissected through a 70 μm nylon cell strainer, washed, RBCs were lysed on ice for 5 minutes using RBC lysis buffer from Sigma-Aldrich. These cells were stained with Live/Dead fixable blue (Life Technologies) to exclude dead cells from analysis before staining with cell surface antibodies. These cells were further fixed and permeabilized with FoxP3 Fix/Perm buffer kit from eBioscience according to the manufacturer's instructions and then stained with intracellular antibodies for further analysis by flow cytometry. Data were acquired on BD LSR II cytometer and analyzed by FlowJo Software.

Human Tumor Analysis

Fresh tumors were manually minced prior to enzymatic digestion with 2 mg/mL collagenase A (Roche, Cat. No. 11-088-793-001) and 40 units/mL DNase-1 (Sigma-Aldrich, Cat. No. D5025) in DMEM and incubated with agitation at 37° C. for 60 min. Following incubation, digests were passed through a 70 μm filter to remove residual particulates.

Cells were then pelleted (centrifugation at 600 g for 5 min), washed in PBS, counted using a Trypan Blue exclusion viability dye, and re-pelleted prior to final resuspension at approximately 1-5 million live cells/mL in cell culture freezing media comprised of 90% FBS and 10% DMSO (Sigma-Aldrich, Cat. No. D2650). Samples immediately underwent controlled freezing (CoolCell LX) to −80° C. before being moved into long-term liquid nitrogen storage.

RNA Extraction from Tumors and Nanostring Analysis

Mice were challenged and treated as described above and humanely killed on day 14 to isolate tumors. Isolated tumors were dissociated in the presence of Trizol reagent in gentleMACS M tubes by using the gentleMACS Dissociators. RNA was further extracted from dissociated tissue using RiboPure RNA purification kit by following the kit manufacturer's protocol. For each Nanostring Assay, total RNA from tumors were incubated overnight with NanoString code set mix at 65 degrees Celsius. NanoString nCounter prep station was then loaded with this reaction mix cartridge for binding and washing. The cartridge was then transferred to the NanoString nCounter digital analyzer for scanning and data collection.

In-Vitro Activation of T Cells

Naïve spleens were isolated from LILRB4 knock-out (KO) and Wild-type (WT) mice. Single-cell suspensions were prepared from spleens, red blood cells were lysed with RBC lysis buffer by incubating it on ice for 5 minutes, and splenocytes were filtered through cell strainers. Naïve untouched total T cells were isolated by using negative T cell isolation kit from Stemcell technologies. $5 \times 7 \times 10^4$ naïve T cells were stimulated in-vitro in a 96-well round bottom plate with anti-CD3 (1.25 µg/ml) and anti-CD28 (1.25 µg/ml) antibodies for 72 hours. 0.5 µl/ml of monensin (BD Biosciences) and 0.5 µl/ml of brefeldin A (BD Biosciences) were added during the final 4 h of stimulation. Cells were then stained for surface and these cells were further fixed and permeablized with FoxP3 Fix/Perm buffer kit from eBioscience according to the manufacturer's instructions and then stained with intracellular antibodies for further analysis by flow cytometry.

Generation of Anti-LILRB4 Monoclonal Antibody

LILRB4 peptide-KLH was used to immunize Armenian hamster. Fusions are performed in Iscove's DMEM supplemented with 20% FBS, 1 mM sodium pyruvate, 4 mM L-glutamine, 50 U/ml Penicillin, 50 ug/ml streptomycin, 50 uM 2-ME and 1% Hybridoma Cloning Factor and selected by HAT(hypoxanthine-aminopterin-thymidine) medium. Primary method of screening of hybridoma supernatants was Elisa using peptide-BSA and selected hybridomas were then screened with flow cytometry for binding to LILRB4-overexpressed cells. For flow screening, LILRB4-overexpressed cells and parental CHO cells were stained with LILRB4 antibody or culture supernatants at 4° C. for 30 minutes. These cells were washed twice with FACS buffer and stained with anti-armenian hamster secondary antibody conjugated with PE at 4° C. for 30 minutes for further analysis by flow cytometry.

Mass Cytometry Antibodies

Metal conjugated antibodies were purchased from Fluidigm or unlabeled antibodies were purchased from various vendors and conjugated with metals in-house as per manufacturer's protocol (Fluidigm). Appropriate dilutions of each antibody were determined by serial dilutions of each antibody and staining relevant biological samples. The ideal dilution of each antibody was then identified after staining analysis to minimize background and optimize detection of positively expressing populations.

Mass Cytometry Analysis

Cryopreserved melanoma tumor digests and murine tumor digests (as described above) were thawed and mashed through 70 µm filters into RPMI-1640 with 10% FBS and P/S. Single cell suspensions were then purified on a Histopaque-1119 (Sigma-Aldrich) discontinuous gradient centrifuged at 2000 rpm for 20 minutes at room temperature. Live cells were then washed twice with FACS buffer and total concentration determined. $2.5 \times 10^6$ cells obtained from tumors were then incubated with blocking buffer containing 2% of each bovine, murine, rat, hamster, and rabbit serum and 25 µg/ml of 2.4G2 antibody at 4° C. for 10 minutes prior to surface staining with antibody cocktail at 4° C. for 30 minutes. Cells were then incubated with 195Pt cisplatin at 4° C. for 1 minute, washed twice with FACS buffer and barcoded using palladium metal barcoding reagents according to the manufacturer's protocol (Fluidigm). Cells were then fixed and permeabilized using the FoxP3 permeabilization kit (eBioscience) and stained with intracellular stain antibody cocktail for 30 minutes at room temperature. These stained cells were then washed twice with FoxP3 permeabilization buffer and twice with FACS buffer and were incubated overnight in 1.6% PFA-PBS with Iridium nucleic acid intercalator. These cells were then washed with 0.5% BSA-PBS, filtered, and washed twice with 0.10% BSA water prior to analysis. Samples were then acquired using Helios mass cytometer using the Helios6.5.358 acquisition software (Fluidigm). Mass cytometry data were normalized to EQ 4-element bead signal using normalization software (Fluidigm) and mass tag barcodes were resolved using Debarcoder (Fluidigm). Samples were then manually gated for event length, live/dead discrimination, particular population etc. in FlowJo. Data were then exported for downstream analysis and t-SNE (t-Distributed Stochastic Neighbor Embedding) dimension reduction and Phonograph clustering analyses was done by using Cyt tool in MATLAB software.

Statistical Analysis

Data were analyzed with the GraphPad Prism 6.0 software program. The Student's t-test was used to assess differences between two groups for statistical significance. The Kaplan-Meier method was used to analyze survival data, and the log-rank (Mantel-Cox) test was used to assess differences in survival between different groups for statistical significance. P values <0.05 were considered statistically significant.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publication No. US20050214860
U.S. Patent Application No. 2004/0126828
U.S. Patent Application No. 2002/0172677
U.S. Pat. No. 6,891,024
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,469,797
U.S. Pat. No. 4,472,509
U.S. Pat. No. 4,606,855
U.S. Pat. No. 4,703,003
U.S. Pat. No. 4,742,159
U.S. Pat. No. 4,767,720
U.S. Pat. No. 4,816,567
U.S. Pat. No. 4,867,973
U.S. Pat. No. 4,938,948
U.S. Pat. No. 4,946,778
U.S. Pat. No. 5,021,236
U.S. Pat. No. 5,091,513
U.S. Pat. No. 5,164,296
U.S. Pat. No. 5,196,066
U.S. Pat. No. 5,223,409
U.S. Pat. No. 5,403,484
U.S. Pat. No. 5,420,253
U.S. Pat. No. 5,565,332
U.S. Pat. No. 5,571,698
U.S. Pat. No. 5,627,052
U.S. Pat. No. 5,656,434
U.S. Pat. No. 5,770,376
U.S. Pat. No. 5,789,208
U.S. Pat. No. 5,821,337
U.S. Pat. No. 5,844,091
U.S. Pat. No. 5,858,657
U.S. Pat. No. 5,861,155
U.S. Pat. No. 5,871,907
U.S. Pat. No. 5,969,108
U.S. Pat. No. 6,054,297
U.S. Pat. No. 6,165,464
U.S. Pat. No. 6,365,157
U.S. Pat. No. 6,406,867
U.S. Pat. No. 6,709,659
U.S. Pat. No. 6,709,873
U.S. Pat. No. 6,753,407
U.S. Pat. No. 6,814,965
U.S. Pat. No. 6,849,259
U.S. Pat. No. 6,861,572
U.S. Pat. No. 6,875,434
U.S. Pat. No. 6,881,557
U.S. Pat. No. 6,946,546

Remington's Pharmaceutical Sciences 22$^{nd}$ edition, 2012.

Boj et al., Organoid models of human and mouse ductal pancreatic cancer. Cell. 2015; 160(1-2):324-38.

Foster et al. Characterization of prostatic epithelial cell lines derived from transgenic adenocarcinoma of the mouse prostate (TRAMP) model. Cancer Res. 1997; 57(16): 3325-30.

van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med 1999: 190(3):355-66.

What is claimed is:

1. An isolated monoclonal antibody, wherein the antibody specifically binds to LILRB4 and comprises:

(I)
   (a) a first V$_H$ CDR of SEQ ID NO: 1 (GFMFSSYW);

(b) a second V$_H$ CDR of SEQ ID NO: 2 (INKDVTTT);

(c) a third V$_H$ CDR of SEQ ID NO: 3 (VRNHGSRYAYFDV);

(d) a first V$_L$ CDR of SEQ ID NO: 4 (TQHRTFY);

(e) a second V$_L$ CDR of SEQ ID NO: 5 (VNSDGSQ); and (f) a third V$_L$ CDR of SEQ ID NO: 6 (GVNYESGKQYGYV).

2. The antibody of claim 1, wherein the antibody comprises a V$_H$ domain at least about 80% identical to the V$_H$ domain of SEQ ID NO: 10 and a V$_L$ domain at least about 80% identical to the V$_L$ domain of SEQ ID NO: 11.

3. The antibody of claim 2, wherein the antibody comprises a V$_H$ domain identical to the V$_H$ domain of SEQ ID NO: 10 and a V$_L$ domain identical to the V$_L$ domain of SEQ ID NO: 11.

4. The antibody of claim 1, wherein the antibody is recombinant.

5. The antibody of claim 1, wherein the antibody is an IgG, IgM, IgA or an antigen binding fragment thereof.

6. The antibody of claim 1, wherein the antibody is a Fab', a F(ab')2, a monovalent scFv, or a bivalent scFv.

7. The antibody of claim 1, wherein the antibody is a humanized antibody or de-immunized antibody.

8. The antibody of claim 1, wherein the antibody is conjugated to an imaging agent, a chemotherapeutic agent, a toxin or a radionuclide.

9. A composition comprising an antibody of claim 1 in a pharmaceutically acceptable carrier.

10. An isolated polynucleotide molecule comprising a nucleic acid sequence encoding an antibody of claim 1.

11. A recombinant polypeptide comprising an antibody V$_H$ domain comprising CDRs 1-3 of the V$_H$ domain of SEQ ID NOs: 1, 2, and 3 and an antibody V$_L$ domain comprising CDRs 1-3 of the V$_L$ domain of SEQ ID NOs: 4, 5, and 6.

12. An isolated polynucleotide molecule comprising a nucleic acid sequence encoding a polypeptide of claim 11.

13. A host cell comprising one or more polynucleotide molecule(s) of claim 12.

14. The host cell of claim 13, wherein the host cell is a mammalian cell, a yeast cell, a bacterial cell, a ciliate cell or an insect cell.

15. A method for treating cancer in a subject comprising administering an effective amount of an antibody that specifically binds to LILRB4 and comprises:

(I)
   (a) a first V$_H$ CDR of SEQ ID NO: 1 (GFMFSSYW);

(b) a second V$_H$ CDR of SEQ ID NO: 2 (INKDVTTT);

(c) a third V$_H$ CDR of SEQ ID NO: 3 (VRNHGSRYAYFDV);

(d) a first V$_L$ CDR of SEQ ID NO: 4 (TQHRTFY);

(e) a second V$_L$ CDR of SEQ ID NO: 5 (VNSDGSQ); and (f) a third V$_L$ CDR of SEQ ID NO: 6 (GVNYESGKQYGYV).

16. The method of claim 15, wherein the cancer is leukemia, breast cancer, melanoma, prostate cancer, or pancreatic cancer.

17. The method of claim 15, wherein the antibody is administered intravenously, intradermally, intratumorally, intramuscularly, intraperitoneally, subcutaneously, or locally.

18. The method of claim 15, further comprising administering at least a second anticancer therapy to the subject.

19. The method of claim 18, wherein the second anticancer therapy is a surgical therapy, chemotherapy, radiation therapy, cryotherapy, hormonal therapy, immunotherapy or cytokine therapy.

20. The method of claim 15, wherein the treatment of cancer comprises treatment of a solid tumor.

* * * * *